(12) United States Patent
Py

(10) Patent No.: US 6,739,636 B2
(45) Date of Patent: May 25, 2004

(54) CONTACT LENS APPLICATOR AND CARTRIDGE USED IN CONNECTION THEREWITH

(75) Inventor: Daniel Py, Stamford, CT (US)

(73) Assignee: Medical Instill Technologies, Inc., Stamford, CT (US)

( * ) Notice: Subject to any disclaimer, the term of this patent is extended or adjusted under 35 U.S.C. 154(b) by 0 days.

(21) Appl. No.: 10/139,192

(22) Filed: May 2, 2002

(65) Prior Publication Data

US 2002/0163212 A1 Nov. 7, 2002

Related U.S. Application Data

(60) Provisional application No. 60/288,030, filed on May 2, 2001.

(51) Int. Cl.[7] .................................................. A61F 9/00
(52) U.S. Cl. ............................................ 294/1.2; 206/5.1
(58) Field of Search ........................ 294/1.2; 206/5.1; 606/107

(56) References Cited

U.S. PATENT DOCUMENTS

| | | | |
|---|---|---|---|
| 2,919,696 A | | 1/1960 | Rinaldy |
| 3,091,328 A | * | 5/1963 | Leonardos .................. 206/5.1 |
| 3,139,298 A | | 6/1964 | Grabiel |
| 3,304,113 A | | 2/1967 | Hutchison |
| 3,879,076 A | | 4/1975 | Barnett |
| 3,910,618 A | | 10/1975 | Massenz |
| 4,037,866 A | | 7/1977 | Price |
| 4,071,272 A | | 1/1978 | Drdlik |
| 4,093,291 A | | 6/1978 | Schurgin |
| 4,113,297 A | | 9/1978 | Quinn |
| 4,200,320 A | | 4/1980 | Durham |
| 4,201,408 A | | 5/1980 | Tressel |
| 4,244,466 A | | 1/1981 | Arnhem |
| 4,308,947 A | | 1/1982 | Arnhem |

(List continued on next page.)

FOREIGN PATENT DOCUMENTS

| | | |
|---|---|---|
| DE | 3822654 A1 | 1/1990 |
| DE | 3920919 A1 | 1/1990 |
| FR | 2496906 | 6/1982 |
| FR | 2525472 | 10/1983 |
| GB | 2001778 A | 2/1979 |
| JP | 61018920 | 1/1986 |
| JP | 02023960 | 1/1990 |
| WO | WO 81/02287 | 8/1981 |
| WO | WO 93/04648 | 3/1993 |
| WO | WO 01/10367 | 8/2000 |

*Primary Examiner*—Dean J. Kramer
(74) *Attorney, Agent, or Firm*—McCarter & English, LLP

(57) ABSTRACT

A contact lens applicator has an elongated housing defining an interior chamber for storing contact lenses, first and second triggers mounted on the housing, a depressor for depressing each eyelid where the depressor is drivingly coupled to the triggers, a pair of opposing wing-shaped members projecting outwardly from opposite sides of the rollers for providing a support surface for facilitating locating the apparatus over the eye, and a pusher assembly slidably mounted within the interior chamber for engaging a contact lens holder and applying a contact lens thereon to the eye when the triggers are actuated. The contact lens is stored in a cartridge within the elongated housing. The lens holder is movable within the cartridge upon actuating the pusher, and includes a predetermined amount of saline or other solution for defining appropriate conditions for storing the lens.

61 Claims, 19 Drawing Sheets

U.S. PATENT DOCUMENTS

| | | |
|---|---|---|
| 4,378,126 A | 3/1983 | Procenko |
| 4,387,921 A | 6/1983 | Licata |
| 4,565,396 A | 1/1986 | Larimer |
| 4,792,334 A | 12/1988 | Py |
| 4,908,024 A | 3/1990 | Py |
| 4,946,452 A | 8/1990 | Py |
| 4,981,479 A | 1/1991 | Py |
| 5,069,494 A | 12/1991 | Reinson et al. |
| 5,085,651 A | 2/1992 | Py |
| 5,133,702 A | 7/1992 | Py |
| 5,163,929 A | 11/1992 | Py |
| 5,246,259 A | 9/1993 | Hellenkamp et al. |
| 5,267,986 A | 12/1993 | Py |
| 5,300,115 A | 4/1994 | Py |
| 5,320,845 A | 6/1994 | Py |
| 5,366,499 A | 11/1994 | Py |
| 5,401,259 A | 3/1995 | Py |
| 5,407,241 A | 4/1995 | Harrison |
| 5,538,301 A | 7/1996 | Yavitz et al. |
| 5,558,374 A | 9/1996 | Harrison |
| 5,613,957 A | 3/1997 | Py |
| 5,649,727 A * | 7/1997 | St. Louis ..................... 294/1.2 |
| 5,685,869 A | 11/1997 | Py |
| 5,688,007 A | 11/1997 | Jefferson |
| 5,695,049 A * | 12/1997 | Bauman ..................... 206/5.1 |
| 5,732,990 A | 3/1998 | Yavitz et al. |
| 5,875,931 A | 3/1999 | Py |
| 5,913,556 A | 6/1999 | Perusse |
| 5,944,702 A | 8/1999 | Py |
| 6,033,384 A | 3/2000 | Py |
| RE37,047 E | 2/2001 | Py |
| 6,213,982 B1 | 4/2001 | Py |
| 6,401,915 B1 * | 6/2002 | Faxe ......................... 206/5.1 |

* cited by examiner

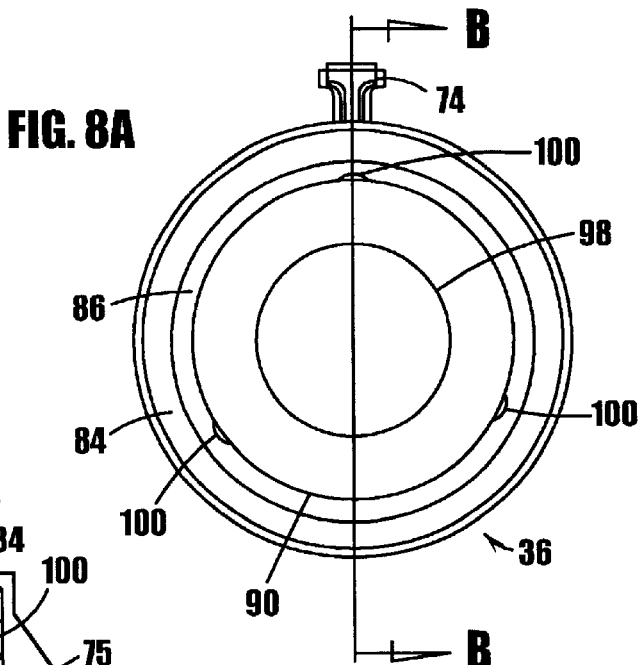
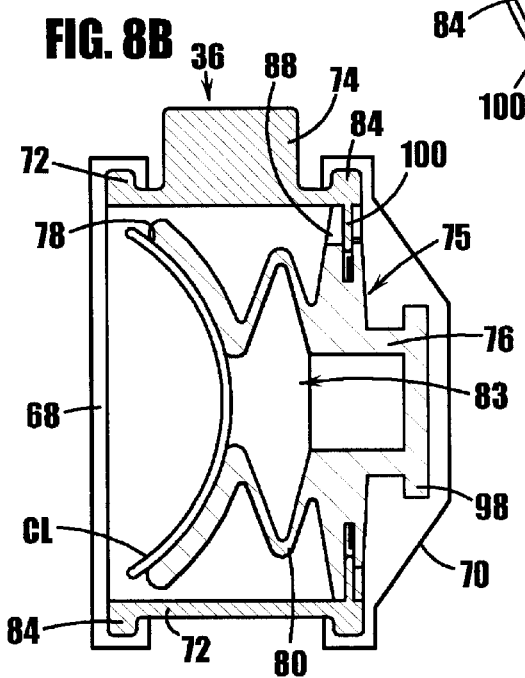
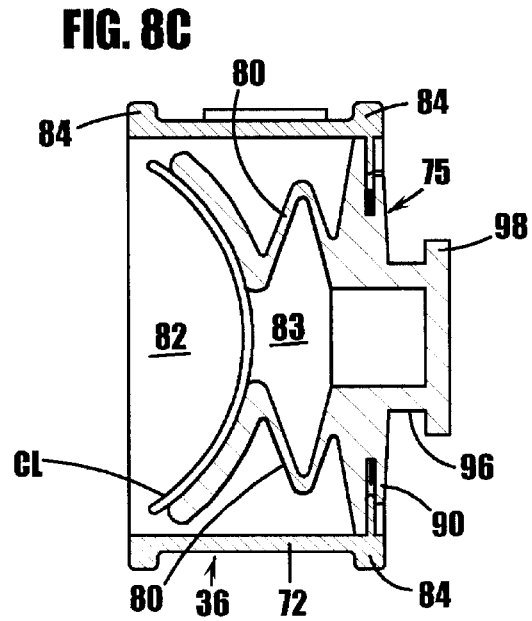
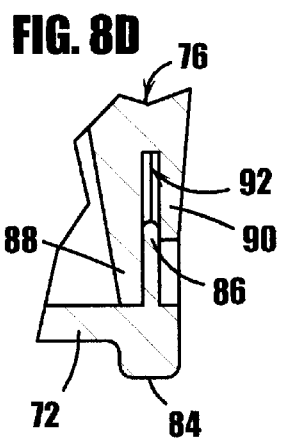

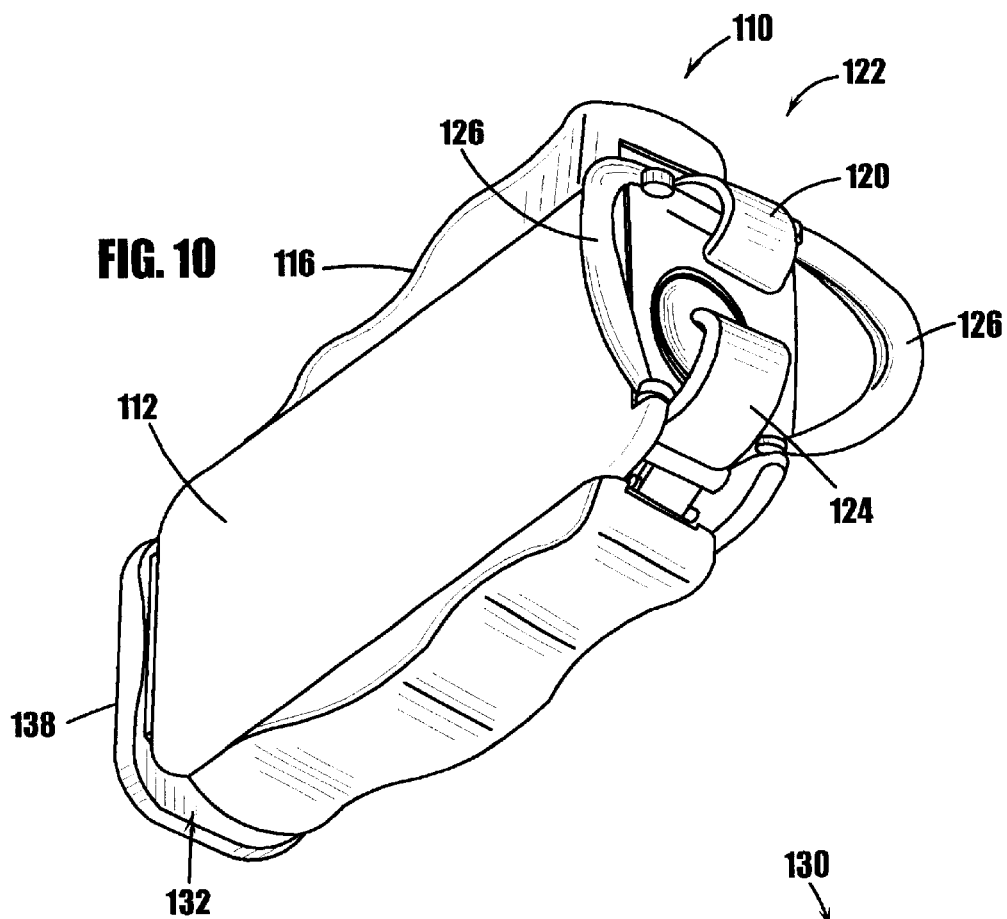
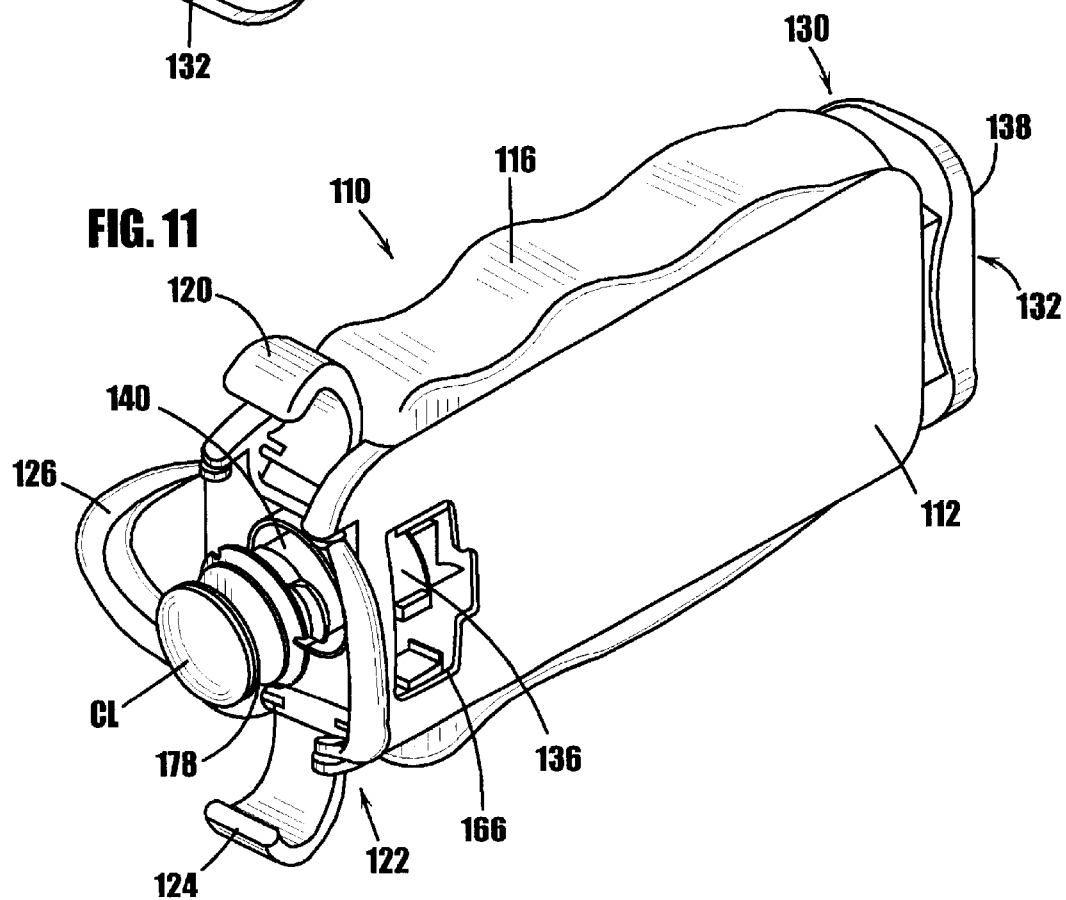

CONTACT LENS APPLICATOR AND CARTRIDGE USED IN CONNECTION THEREWITH

CROSS-REFERENCE TO RELATED APPLICATION

This application claims priority to U.S. Provisional Patent Application Ser. No. 60/288,030, filed May 2, 2001, which is incorporated herein by reference.

FIELD OF THE INVENTION

The present invention relates to ocular treatment apparatus, and more particularly to such apparatus for storing and applying contact lenses to a person's eye.

BACKGROUND INFORMATION

Many patients who require optical correction for visual acuity wear eye-glasses because they either cannot, or do not desire to apply contact lenses to their eyes. Among those who are able to apply contact lenses to their eyes without assistance, it is believed that approximately 25% of these patients have terminated use of contact lenses because of complications arising from a lack of aseptic conditions and/or because of frustrations or difficulties arising from the need to clean and store the contact lenses, and transport with themselves the necessary containers and cleaning solutions to maintain the contact lenses. For example, the containers for holding contact lenses need to be carefully cleaned and are difficult, and in many cases, impossible to adequately clean. In addition, these persons typically require a mirror to apply the contact lenses, and because they have difficulty viewing themselves within the mirror without eyeglasses, they have further difficulty applying the contact lenses to their eyes without assistance.

Many ocular complications relating to contact lenses are due to infections and/or toxic reactions arising from incomplete rinsing of the contact lenses with cleaning solutions or otherwise inadequate cleaning or not maintaining the sterile conditions of the lenses prior to application to the eyes. A certain number of such complications are due to the preservatives contained within the cleaning solutions. For example, it has been widely demonstrated that certain preservatives are aggressive, irritating and/or damaging to the superficial layers of the cornea of the eye.

There are numerous events that must be carried out to properly apply contact lenses to a person's eyes, including: forcing the upper and lower eyelids in a wide-open position so that the contact lens (typically about 14.5 mm in outer diameter) can fit through the opening between the eyelids; adequately cleaning the finger(s) used to handle and apply the contact lens; making sure the contact lens is properly oriented with the correct side (or concave side) facing the eye; making sure the contact lens is in a state of equilibrium on the finger at the time of application; and applying the contact lens onto the cornea of the eye without irritating the cornea or otherwise causing the eye to blink during application. The sensitivity of the cornea is among the highest of the human tissues, and therefore if the eyelids are not maintained in the proper position during application of the contact lens, the maneuver fails.

In view of the above, several attempts have been made to aid a person when applying a contact lens. For example, U.S. Pat. No. 2,919,696 to Rinaldy shows an instrument for applying a contact lens. The instrument has a cup member 11 with a rim 13. A bracket 14 supports a lens supporting element 20 which is slidably mounted within the cup member 11. In use, the lens supporting element 20 is retracted and retains the lens by surface tension. The rim 13 is manually deformed and placed against the eyelids so that upon relaxing the rim 13, the eyelids are retained open. Subsequently, the lens supporting element 20 is depressed to place the contact lens on the eye and the instrument is removed.

U.S. Pat. No. 3,910,618 to Massenz provides a contact lens applicator having a cup 11 connected to an irrigation bottle 23 by a tube 14. The tube 14 slides within the cup 11 and communicates fluid into the cup 11 from the irrigation bottle 23. The end of the tube within the cup 11 has a lens seat 19 for receiving a contact lens. The distal end of the cup 11 is a rim 12. Both the rim 12 and the cup are made of rubber. In operation, the rim 12 is squeezed to bring the outer edges together. The rim 12 is applied to the eyelid. Upon relief of the compression, the cup 11, being resilient, resumes shape keeping the eye widely exposed. Then, the tube 14 is moved toward the eye to place a contact lens thereon and the irrigation bottle 23 provides fluid as desired.

U.S. Pat. No. 4,113,297 to Quinn illustrates a device for inserting and removing a contact lens 32. A stand 11 supports the device upright on a flat surface. A storage chamber 15 is in fluid communication with a float chamber 14. An applicator eyepiece 16 mounts on top of the float chamber 14 and defines an aperture. A rod member 20 extends through the aperture and receives a contact lens on its top. The height of the rod member 20 is determined by the fluid level within the float chamber 14. Actuation of a flexible portion of the storage chamber 15 varies the fluid level within the float chamber 14 and, thus, the height of the rod member 20. To apply a contact lens, the fingers of one hand are used to hold the eye open over the eyepiece 16. The free hand actuates the storage chamber 15 to raise the rod member 20 to place the contact lens on the eye.

U.S. Pat. No. 5,069,494 to Reinson et al. shows a contact lens applicator 25 which also stores a plurality of contact lens. The container portion 10 includes multiple portions 10 which are identical and interlocking. Each portion 10 contains a single contact lens disposed in a liquid. The lens is supported on a deformable projection made of five legs 20. The portions 10 have a cover surface 16 and sidewalls with inner threads 13 and outer threads 14. The inner threads 13 and outer threads 14 of adjacent portions 10 threadably engage such that the adjacent portion 10 defines the cover for the next adjacent portion 10. A base 12 upon which the contact lens rests completes the portions 10.

There are problems associated with each of these prior art inventions such as contamination from fingers or the device itself, a significant skill level being required to insert a lens, no self-contained storage means, and no means to engage and retain the eyelids open simultaneously with the insertion of the lens. Accordingly, it is an object of the present invention to provide a contact lens applicator and cartridge used in connection therewith that overcomes many of these or other problems, drawbacks and/or disadvantages associated with applying and storing contact lenses.

SUMMARY OF THE INVENTION

The present invention is directed to a contact lens applicator comprising a housing assembly including a hollow, elongated housing and at least one trigger pivotally mounted on the housing. A first eyelid depressor or like means for depressing an eyelid is movably mounted on one end of the housing, and is drivingly coupled to the trigger for moving the first eyelid depressor upon depressing or otherwise actuating the trigger. Preferably, a second eyelid depressor or like means for depressing another eyelid is movably mounted on the same end of the housing, and is spaced apart from the first eyelid depressor for engaging the facial tissue adjacent to the other eyelid. The second eyelid depressor is drivingly coupled to the trigger for moving the second eyelid depressor upon depressing or otherwise actuating the trigger. In the currently preferred embodiments of the present invention, the eyelid depressors may take the form of rollers rotatably mounted on the housing or cantilevers pivotally mounted on the housing. A pair of wing-shaped members project outwardly from opposite sides of the eyelid depressors relative to each other, and each defines a support surface for contacting the facial tissue surrounding a person's eye to, in turn, facilitate locating the applicator over the eye and applying a contact lens thereto. Preferably, the wing-shaped members define the shape of a typical eyecup for comfortably engaging the facial tissue surrounding the eye. A pusher is slidably mounted within the housing, and is drivingly connected to the trigger for moving the pusher within the housing upon depressing or otherwise actuating the trigger.

In one embodiment of the invention, the applicator further comprises at least one cartridge for holding a contact lens, and which is receivable within the applicator to dispense the lens therefrom onto a person's eye. Preferably, the cartridge defines a vial or like enclosure for receiving therein the lens, and includes a predetermined amount of saline or other solution within the vial for defining appropriate conditions for storing the lens. A relatively soft, flexible contact lens holder is mounted within the vial, and defines a base, a lens support surface for supporting the lens, and a bellows or like flexible portion extending between the lens support surface and the base. The cartridge preferably further comprises a pair of end caps for sealing the contact lens and saline or other solution within the vial, and which can be removed upon installing the cartridge into the applicator or during insertion of the lens therefrom onto an eye. The housing defines a cartridge chamber for receiving therein the cartridge, and the pusher is movable into the chamber for engaging the base of the cartridge and moving the lens support surface between a retracted position and an extended position for applying the contact lens to an eye.

In the operation of the applicator, a user may place the end of the housing opposite the eyelid depressors onto a table or other support surface with the wing-shaped members facing upwardly. The user then moves the eye intended to receive the contact lens over the eyecup of the applicator so that the wing-shaped portions fit snugly against the facial tissue surrounding the eye. The user then squeezes the trigger which, in turn, moves the first and second eyelid depressors and thereby causes the depressors to engage and move the tissue adjacent to each of the respective eyelids outwardly to retain the eye open during application of the contact lens thereto. Also upon actuating the trigger, the pusher is driven outwardly toward the eye to, in turn, drive the lens support surface from the retracted to the extended position. In the extended position, the lens seated on the lens support surface is gently moved into contact with the eye. If the user looks directly at the lens, the lens is automatically placed onto the exposed cornea of the eye. If, on the other hand, the user looks to one side, the lens is automatically placed onto the eye adjacent to the cornea, and thus onto a less sensitive region of the eye. Upon contacting the cornea with the lens, the pusher continues to move forward a slight distance so that the bellows or like flexible portion of the lens holder is gently deformed. The deformation or contraction of the bellows causes the saline or other solution within the bellows to flow outwardly between the convex lens surface and concave lens support surface and, in turn, facilitates the release and transfer of the lens onto the user's eye. Preferably, the lens support surface defines a plurality of ribs or other protuberances for facilitating the flow of saline or other solution between the lens and lens support surface upon depressing the bellows of the lens holder.

One advantage of the contact lens applicator of the present invention is that the applicator allows a person to overcome the anxiety or fear that otherwise might be associated with performing the intricate motions otherwise required to apply contact lenses to the eyes. Another advantage of the contact lens applicator of the present invention is that the applicator automatically performs all requisite steps for applying contact lenses to the eyes, including opening the eyelids, maintaining the lens in the proper orientation, transferring the lens to the eye, etc. Yet another advantage of the contact lens applicator of the present invention is that the lens is easily maintained sterile throughout application, and there is no need for a person to touch the lens. Another advantage of the contact lens applicator of the invention is that the application of the contact lens may be painless and without any reasonable risk to the cornea. Yet another advantage of the contact lens applicator of the invention is that persons with poor vision can apply the lenses without glasses or mirrors, and therefore may avoid additional drawbacks associated with the prior art.

Other objects and advantages of the present invention will become more readily apparent in view of the following detailed description of the preferred embodiments and accompanying drawings.

BRIEF DESCRIPTION OF THE DRAWINGS

FIG. 8A is a front end, elevational view of a cartridge constructed in accordance with the subject disclosure.

FIGS. 8B and 8C are cross-sectional side views of the cartridge of FIG. 8A taken along lines A—A and C—C, respectively.

FIG. 8D is an enlarged localized view of FIG. 8B.

FIG. 10 is a bottom perspective view of another contact lens applicator constructed in accordance with the subject disclosure.

FIG. 11 is a top perspective view of the contact lens applicator of FIG. 10.

DETAILED DESCRIPTION OF THE PREFERRED EMBODIMENTS

Figure 1:
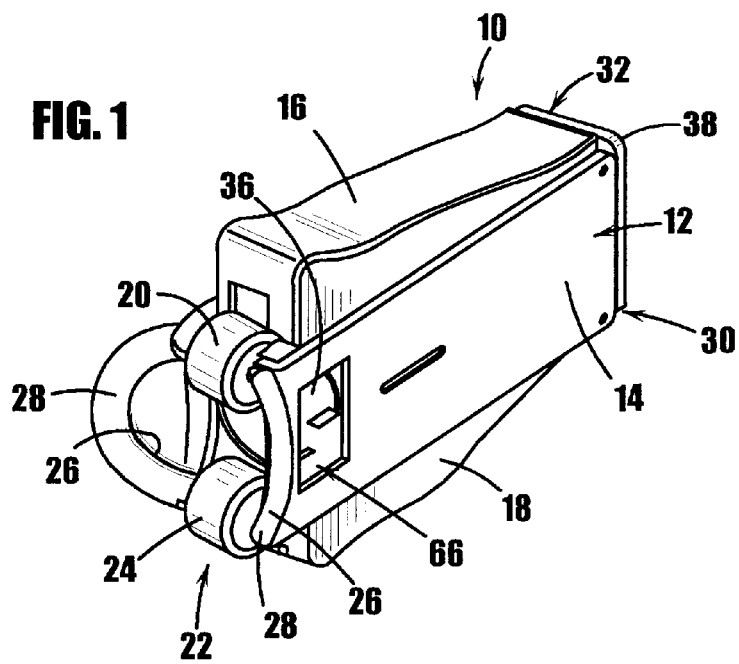
FIG. 1 is a perspective view of a contact lens applicator constructed in accordance with the subject disclosure.

The present invention overcomes many of the prior art problems associated with storing and inserting contact lenses. The advantages, and other features of the applicator disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Figure 2:
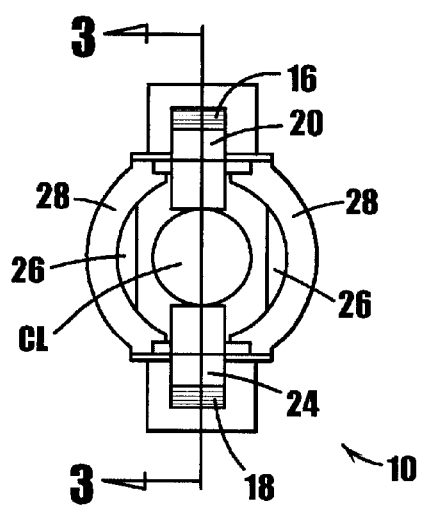
FIG. 2 is a front end, elevational view of the contact lens applicator of FIG. 1.

Referring to FIGS. 1 and 2, a contact lens applicator embodying the present invention is indicated generally by the reference numeral 10. In this double trigger configuration, the contact lens applicator 10 comprises a housing assembly 12 including a hollow, elongated housing 14, a first trigger 16 pivotally mounted on one side of the housing 14, and a second trigger 18 pivotally mounted on an opposite side of the housing 14. A first roller 20 or like means for depressing an eyelid is rotatably mounted on an open proximal end 22 of the housing 14, and is drivingly coupled to the first trigger 16 for moving the first roller 20 upon depressing or otherwise actuating the first trigger 16. A second roller 24 or like means for depressing another eyelid is rotatably mounted opposing the first roller 20 and is spaced apart from the first roller 20 for engaging the facial tissue adjacent to the other eyelid. The second roller 24 is drivingly coupled to the second trigger 18 for moving the second roller 24 upon depressing or otherwise actuating the second trigger 18.

A pair of wing-shaped members 26 project outwardly from opposite sides of the rollers 20, 24 relative to each other, and each defines a support surface 28 for contacting the facial tissue surrounding a person's eye to, in turn, facilitate locating the applicator 10 over the eye and applying a contact lens "CL" (see FIG. 4) thereto. As shown, the wing-shaped members 26 preferably define the shape of a typical eyecup for comfortably engaging the facial tissue surrounding the eye. Preferably, the wing-shaped members 26 are each pivotally mounted to the housing 14 so that they may be folded inwardly for storage and opened outwardly as shown in FIG. 1 for use. As may be recognized by those skilled in the pertinent art based on the teachings herein, the wing-shaped members 26 may be incrementally adjustable to fix the wing-shaped members at any of a plurality of different positions to thereby accommodate user's having different facial dimensions.

Figure 3:
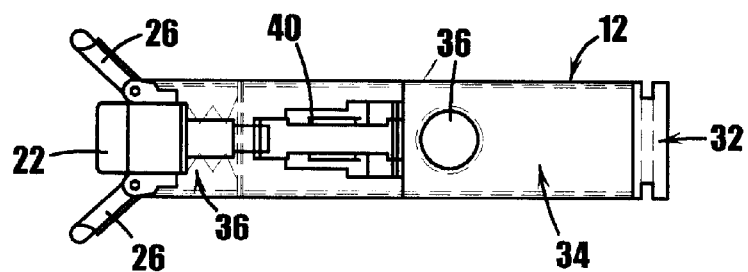
FIG. 3 is a cross-sectional view of the contact lens applicator taken along line 3—3 of FIG. 2.

A distal end 30 of the housing 14 has a base assembly 32 mounted thereon. In one embodiment, the base assembly 32 is snap fit to the housing 14 to allow access to a storage chamber 34 (as shown in FIG. 3) within the housing 14. Typically, cartridges 36 (shown in FIGS. 4 and 7) for storing the contact lenses CL may be contained within the storage chamber 34 of the housing 14. The base assembly 32 also provides a stable platform 38 for standing the elongated housing 14 upright on a substantially flat and level surface, such as a table, to allow unencumbered use of the user's hands.

Figure 4:
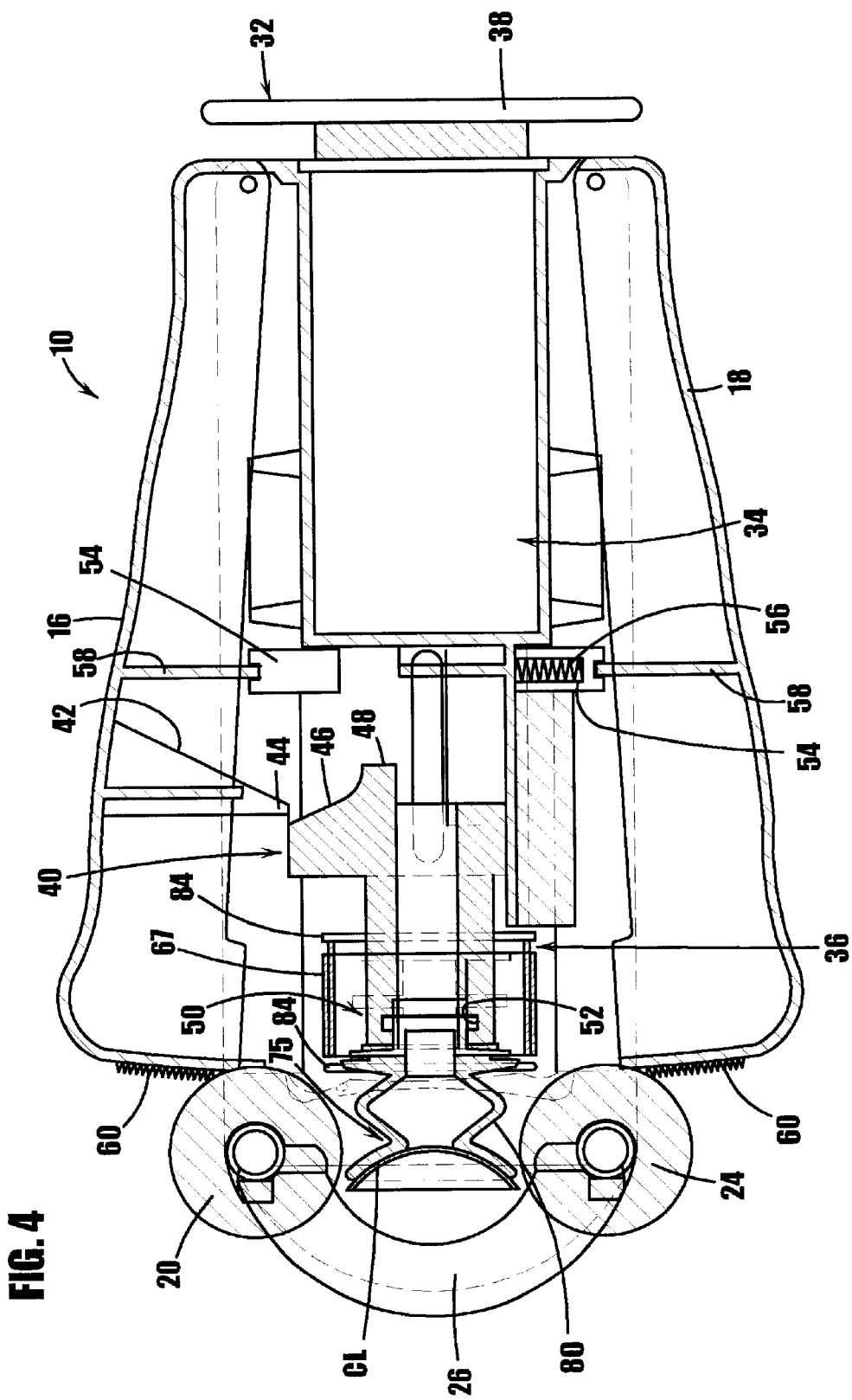
FIG. 4 is a cross-sectional view of the contact lens applicator of FIG. 1 in a retracted position.
Figure 5:
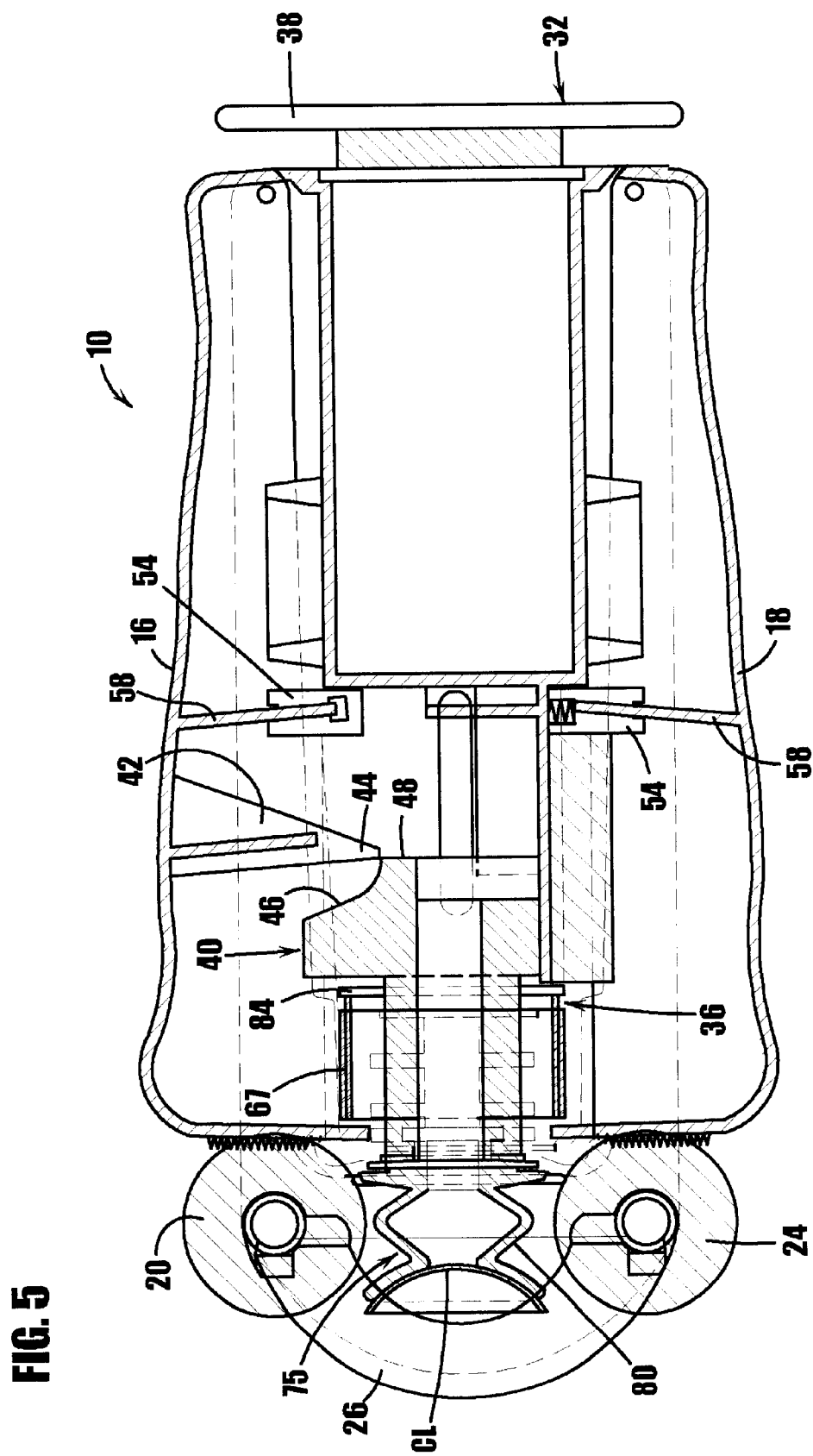
FIG. 5 is a cross-sectional view of the contact lens applicator of FIG. 1 in an extended position.
Figure 6A:
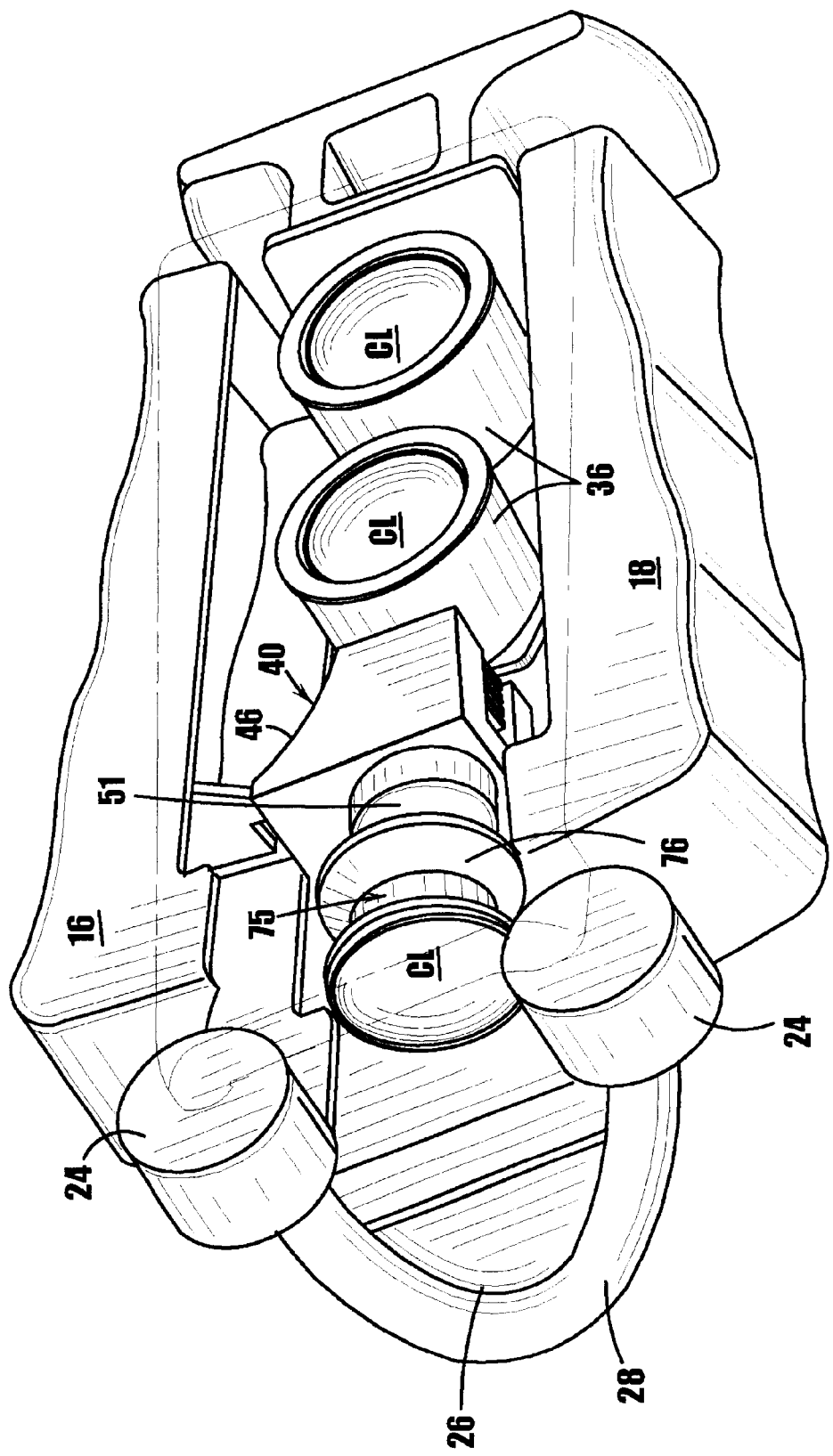
FIGS. 6A and 6B are perspective, partially transparent views of the contact lens applicator corresponding to FIGS. 4 and 5, respectively.
Figure 6B:
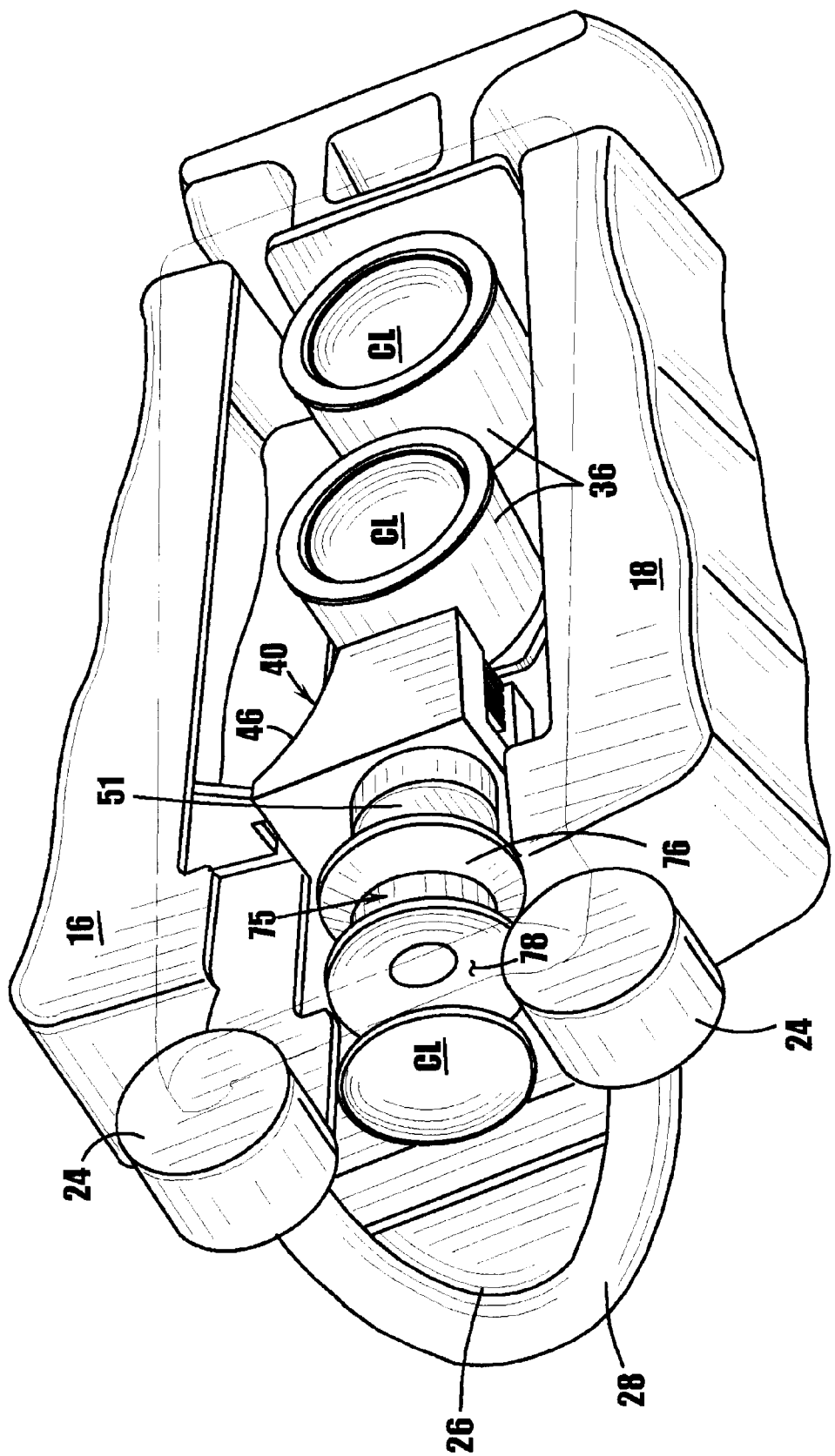

Referring now to FIGS. 3–6B, a pusher 40 is slidably mounted within the housing 14. The pusher 40 is drivingly connected to the first trigger 16 for moving the pusher 40 within the housing 14 upon depressing or otherwise actuating the trigger. As shown in FIGS. 4 and 5, the first trigger 16 includes an actuator 42 projecting inwardly from the trigger 16 and engaging with a free end 44 a cam surface 46 formed on the adjacent end surface of the pusher 40. Upon depressing the trigger 16, the free end 44 of the actuator 42 slides inwardly along the cam surface 46 and, in turn, drives the pusher 40 outwardly towards an extended position. Preferably, the extension of the pusher 40 is limited by the combination of the relative angle of the cam surface 46 and depth within the housing 14 to which the trigger 16 may extend. In another embodiment, the pusher 40 extends until the actuator 42 no longer contacts the cam surface 46, i.e., until the free end 44 of the pusher 40 is located adjacent to the internal end 48 of the pusher 40. As best seen in FIG. 4, a proximal portion 50 of the pusher 40 engages the cartridge 36. Preferably, the proximal portion 50 is tubular shaped, and defines a radially-extending cut-out or recess 51 for laterally receiving one of the cartridges 36. Preferably, an annular channel 52 of the proximal portion 50 releasably locks therein the pusher to the cartridge 36.

Preferably, the triggers 16 and 18 are biased against depression to create a smooth operation thereof and automatic return when released. In a preferred embodiment, the housing 14 has two cylinders 54 for retaining springs 56 (only one shown in FIG. 4) mounted therein. Projections 58 depend inwardly from the triggers 16 and 18 into the cylinders 54 to compress the springs 56 upon actuation and provide a return force when the triggers 16 and 18 are released.

Figure 7:
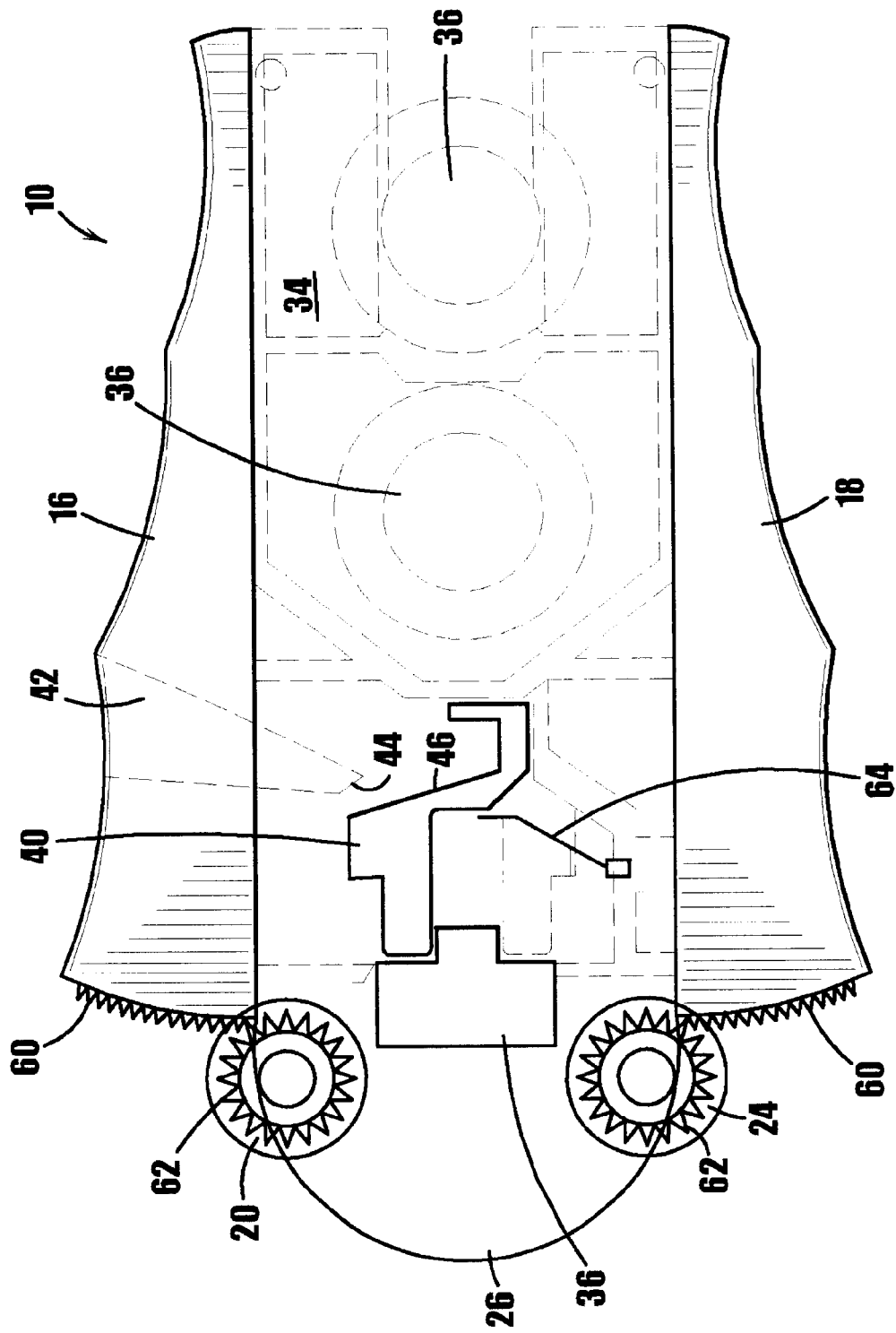
FIG. 7 is a somewhat schematic, cross-sectional view of the contact lens applicator of FIG. 1 showing the bias member mounted within the housing and engaging the pusher for returning the pusher to the retracted position upon releasing the trigger(s) and with other parts removed for clarity.

Referring now to FIG. 7, a rack 60 having a plurality of teeth is disposed on the proximal end of each of the triggers 16 and 18 for engaging a pinion 62 attached to each of the rollers 20 and 24. When the triggers 16 and 18 are depressed, the teeth of the rack 60 mesh with the pinion 62 to force the rotation thereof. A spring or like biasing member 64 is mounted within the housing 14, and the free end of the biasing member 64 engages the pusher 40. Accordingly, upon releasing the trigger 16, the spring 64 drives the pusher 40 rearwardly within the housing 14 into the retracted position and thereby readies the applicator 10 to receive another cartridge and contact lens. Preferably, the biasing member 64 is selected from the group of a leaf spring, coil spring, compressible member and the like as would be appreciated by those of ordinary skill in the pertinent art based upon review of the subject disclosure.

As shown typically in FIG. 1, the housing assembly 12 defines a cartridge chamber 66 for receiving the cartridge 36. When the user is ready to dispense the lens CL from the cartridge 36 onto an eye, the cartridge 36 is removed from the storage chamber 34 of the housing 14. Upon removing a top cover 68 and a bottom cover 70 (see FIG. 8B), solution within the cartridge 36 is permitted to drain out and the cartridge 36 is inserted into the cartridge chamber 66. As shown in FIGS. 4 and 5, the housing 14 includes in this configuration a cartridge mount 67 defining a laterally-extending opening (not shown) for receiving therein the cartridge 36. Preferably, the cartridge mount 67 frictionally engages the side wall of the cartridge 36 therein to releasably secure the cartridge during use. During insertion of a contact lens, a portion of the cartridge 36 is fixed to the pusher 40 and the remainder is fixed to the cartridge mount 67 of the housing 14 as described further below. As may be recognized by those skilled in the pertinent art based on the teachings herein, the cartridge mount need not be accessed from the side of the housing, but may be located and configured in any of numerous different ways. For example, the open end 22 of the housing could be modified to receive the cartridges therein.

Figure 9:
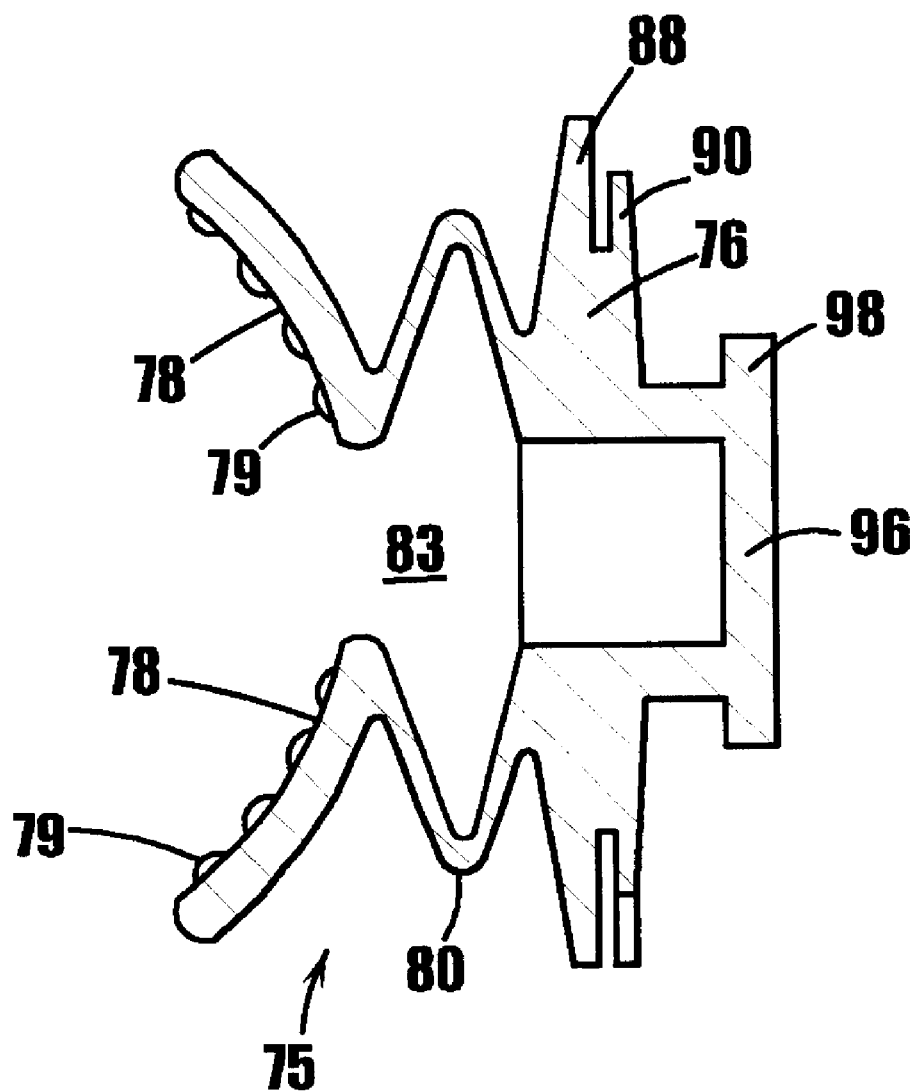
FIG. 9 is a cross-sectional view of a portion of the cartridge of FIG. 8A.
Figure 12:
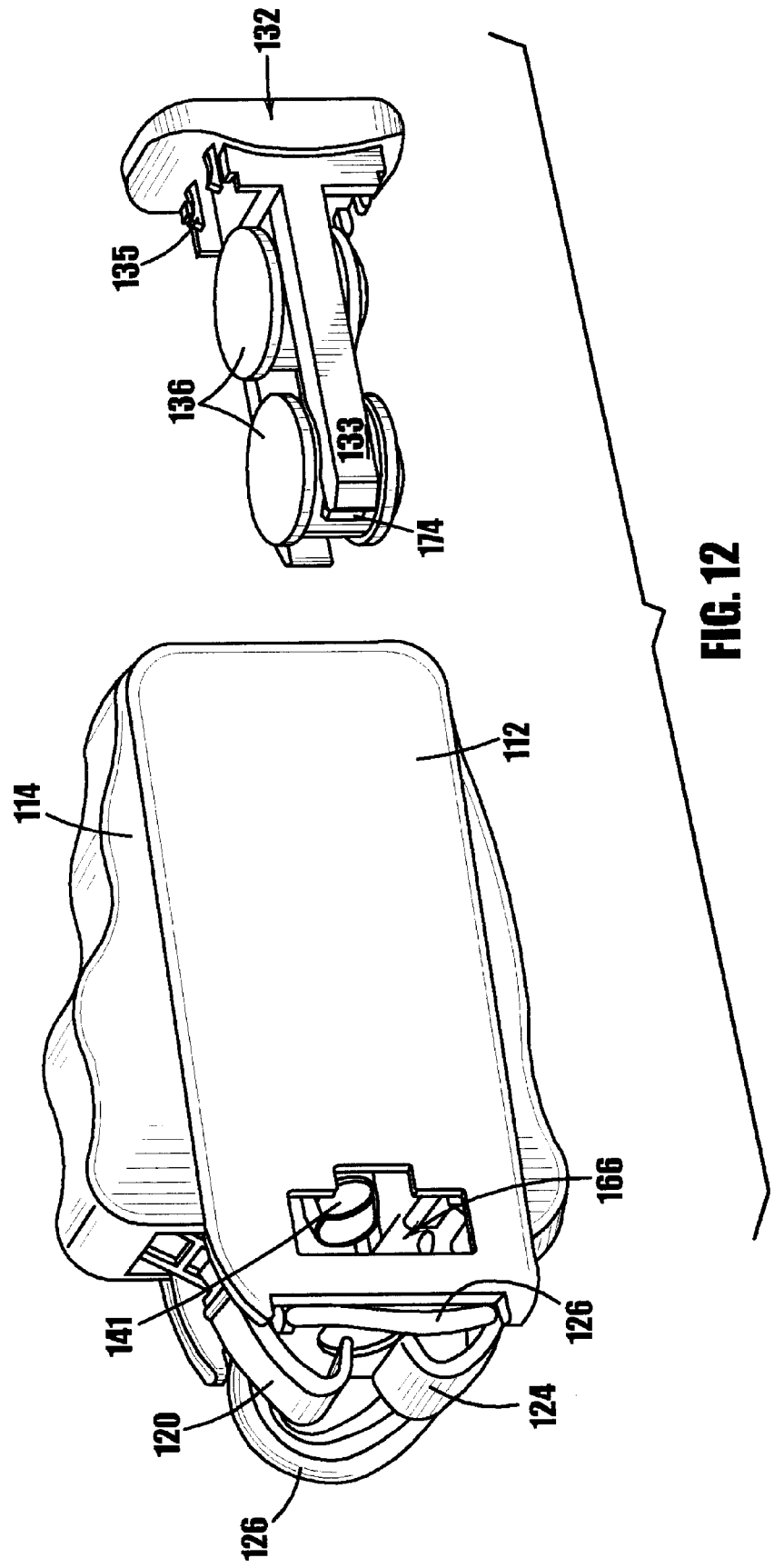
FIG. 12 is a side perspective view of the contact lens applicator of FIG. 10 with the base removed to illustrate two cartridges thereon.

Referring now to FIGS. 8A–D and 9, the cartridge 36 includes a body or vial 72 or like enclosure for receiving therein the lens CL, and a predetermined amount of saline or other solution within the vial 72 for defining appropriate conditions for storing the lens CL. A handle 74 is integral with the vial 72 to facilitate insertion and removal of the vial 72 out of the applicator 10. As best seen in FIG. 9, a relatively soft, flexible contact lens holder 75 is mounted within the vial 72, and defines a base 76, a very soft lens support surface 78 for supporting the contact lens CL, and a bellows or like flexible portion 80 extending between the lens support surface 78 and the base 76 to cushion the impact of the contact lens CL on the eye. As may be recognized by those skilled in the pertinent art based on the teachings herein, the lens holder may be made of any of numerous different materials that are currently or later become known for performing the functions of the lens holder described herein. In the illustrated embodiment, the lens holder is made of a soft, elastomeric material. If desired, the lens support surface may be made softer than the contact lens itself. The vial also defines a cavity 82 for retaining fluid that surrounds the lens holder 75, and the lens holder defines a second cavity 83 within the bellows and underlying the lens also for retaining fluid. The top cover 68 and bottom cover 70 (shown only in FIG. 8B for simplicity) seal the contact lens CL and solution immersing the contact lens CL within the vial 72. During insertion of the cartridge 36 into the cartridge chamber 66, the base 76 is received within the lateral opening 51 of the pusher and engages the annular channel 41 of the pusher to releasably secure the lens holder to the pusher. The proximal portion of the pusher 40 is sized and configured such that the pusher is movable into the vial 72 for forcing the base 76 therethrough, i.e. into the extended position for applying the contact lens CL to an eye, as described further below.

As best shown in FIG. 8B, the ends of the vial 72 define outer collars 84 to sealingly engage the covers 68 and 70 thereto and prevent axial movement of the cartridge when installed within the cartridge mount 67, as shown in FIGS. 4 and 5. As best shown in FIG. 8D, the distal end of the vial 72 forms an inner rib 86 to sealingly engage the base 76. The base 76 includes a pair of annular flanges 88 and 90 defining a channel 92 therebetween, the channel 92 being sized and configured to engage an inner rib 86 of the vial 72. The second annular flange 90 is radially sized to allow axial pressure by the pusher 40 to deflect the flange 90 over the rib 86 and allow the lens holder 75 to extend axially through the vial 72 toward the open proximal end 22 of the applicator 10. As shown in FIGS. 8B and 8C, the base 76 of the lens holder includes a protrusion 96 defining a radially-extending rim 98 adapted to be received within the annular channel 41 of the pusher 40 to releasably lock the lens holder 75 to the pusher 40. As shown in FIGS. 8A and 8B, the annular flange 88 and inner rib 86 each define three aligned apertures forming passages 100 equally spaced relative to each other for allowing fluid to pass therethrough upon removing the bottom cover 70 from the cartridge. Preferably, the cavity 83 of the lens holder 76 retains fluid even after the covers 68 and 70 are removed. It is envisioned that each cartridge 36 may include a designation such as "L" or "R" to indicate which eye the contact lens CL contained therein is destined for. In one embodiment, the cartridge 36 is intended for reuse. In another embodiment, the cartridge is manufactured with a specific contact lens suited to an individual and subsequently disposed after use.

In the operation of the applicator 10, a user preferably places the platform 38 of the base assembly 32 onto a table or other support surface with the wing-shaped members 26 facing upwardly and opened outwardly. A cartridge 36 with the desired contact lens CL is placed on the support surface and the top and bottom covers 68 and 70, respectively, are removed to drain the solution from the chamber 82 and allow inserting the cartridge 36 into the cartridge chamber 66. The radially-extending rim 98 of the base 76 of the cartridge 36 is received through the lateral opening 51 and into the annular channel 41 of the pusher 40 to releasably lock the lens holder 75 to the pusher. In addition, the vial 72 frictionally engages the cartridge mount 67 to releasably secure the cartridge within the housing. The user then moves his or her eye intended to receive the contact lens CL over the wing-shaped members 26 of the applicator 10 so that the support surfaces 28 of the wing-shaped portions 26 fit snugly against the facial tissue surrounding the eye. The user then simultaneously squeezes the first and second triggers 16 and 18, which, in turn, rotate the first and second rollers 20, 24 to cause the rollers 20 and 24 to engage and move the tissue adjacent to each of the respective eyelids outwardly and retain the eye open during application of the contact lens CL thereto. Preferably, the rollers or other eyelid depressors are formed and/or coated with an elastomeric or other non-slip material to facilitate comfortably engaging and/or moving the facial tissue adjacent to the eye. As the pusher is driven outwardly, the second flange 90 of the lens holder deflects over the rib 86 of the vial 72 to allow axial movement thereof. The proximal portion 50 of the pusher 40 extends into the cartridge chamber 66 to drive the lens support surface 78 from the retracted to the extended position.

In the extended position, the contact lens CL seated on the contact lens support surface 78 is gently moved into engagement with the eye. If the user looks directly at the contact lens CL, the contact lens CL is automatically placed onto the exposed cornea of the eye. If, on the other hand, the user looks to one side, the contact lens CL is automatically placed onto the eye adjacent to the cornea, and thus onto a less sensitive region of the eye. Upon engaging the eye with the contact lens CL, the pusher 40 also gently depresses the bellows or like flexible portion 80, which in turn causes the saline or other solution within the bellows chamber 83 and between the contact lens CL and lens support surface 78 to flow outwardly and thereby facilitate release of the contact lens CL therefrom and onto the user's eye. As shown in FIG. 9, the lens support surface 78 preferably defines a plurality of radially and axially spaced protuberances 79 for reducing the surface contact between the lens and support surface and/or for facilitating the flow of saline or other solution therebetween to release the contact lens CL from the lens support surface onto the eye. As may be recognized by those skilled in the pertinent art based on the teachings herein, the lens support surface 78 may take any of numerous different configurations, such as spaced ribs or other configurations, for purposes of reducing the surface contact between the lens and lens support surface, or otherwise facilitating the operation of the applicator.

Referring now to FIGS. 10 and 11, a single trigger embodiment of the contact lens applicator of the present invention is indicated to generally by the reference numeral 110. As will be appreciated by those of ordinary skill in the pertinent art, the applicator 110 utilizes the same principles of the applicator 10 described above. Accordingly, the description is largely directed to the differences for simplicity. The applicator 110 includes a housing 112 having an open proximal end 122 and a distal end 130 enclosed by a removable base assembly 132 defining a support platform 138. A lens support surface 178 (FIG. 11) retains the contact lens CL adjacent to the open proximal end 122. A pusher 140 housed within the interior of the housing 112 is movable between the retracted position of FIG. 10 and the extended position of FIG. 11. The pusher 140 extends the lens support surface 178 and thereby the contact lens CL into the eye. A single trigger 116 mounted to the housing 112 actuates the pusher 140. A pair of wing-shaped or arcuate bands 126 are pivotally mounted about the open proximal end 122 and define support surfaces allowing the applicator 110 to be located comfortably against the corners of the user's eye. The applicator 110 also includes means for depressing the user's eyelids and/or for retaining the eyelids open upon applying a contact lens CL to the user's eye. In the illustrated embodiment, this means takes the form of a pair of curved cantilevers 120 and 124 pivotally mounted to the open proximal end 122 of the housing 112. Preferably, the curved cantilevers 120 and 124 are operatively connected to the single trigger 116 such that as the trigger 116 moves the pusher 140, the curved cantilevers 120 and 124 are substantially simultaneously actuated to move the facial tissues adjacent to the eyelids outwardly and retain the eye open during application of the contact lens CL thereto.

Referring now to FIGS. 12–15, the applicator 110 defines an aperture 166 for receiving a contact lens cartridge 136. Preferably, the contact lens cartridge 136 includes a lens holder 175 defining a lens supporting surface 178 and a base 176 which engages the pusher 140. The base assembly 132 includes a flexible sleeve 133 for retaining multiple contact lens cartridges 136 within the interior of the housing 112 of the applicator 110.

Figure 13:
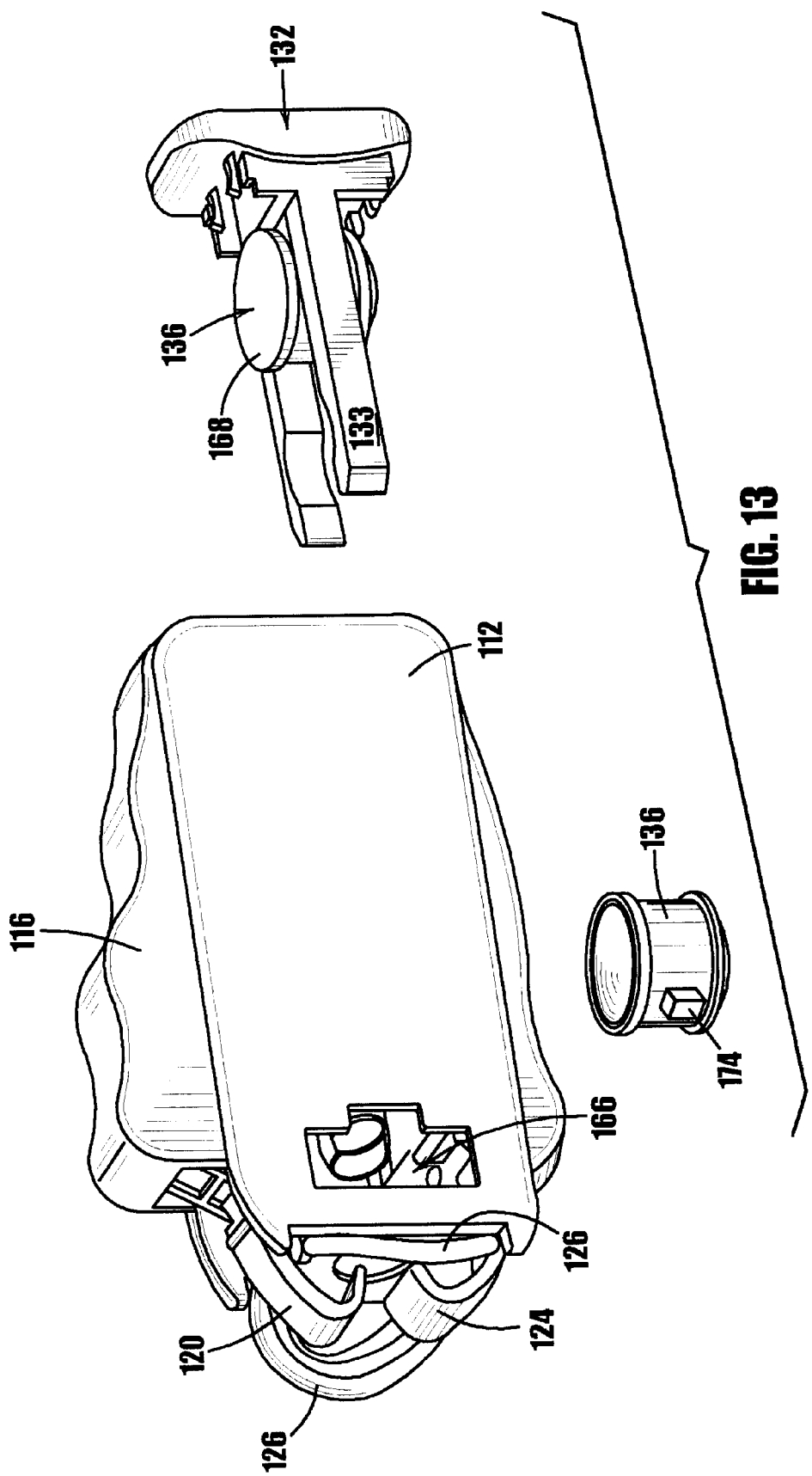
FIG. 13 is a side perspective view of the contact lens applicator of FIG. 10 with a cartridge prepared for insertion therein.
Figure 14:
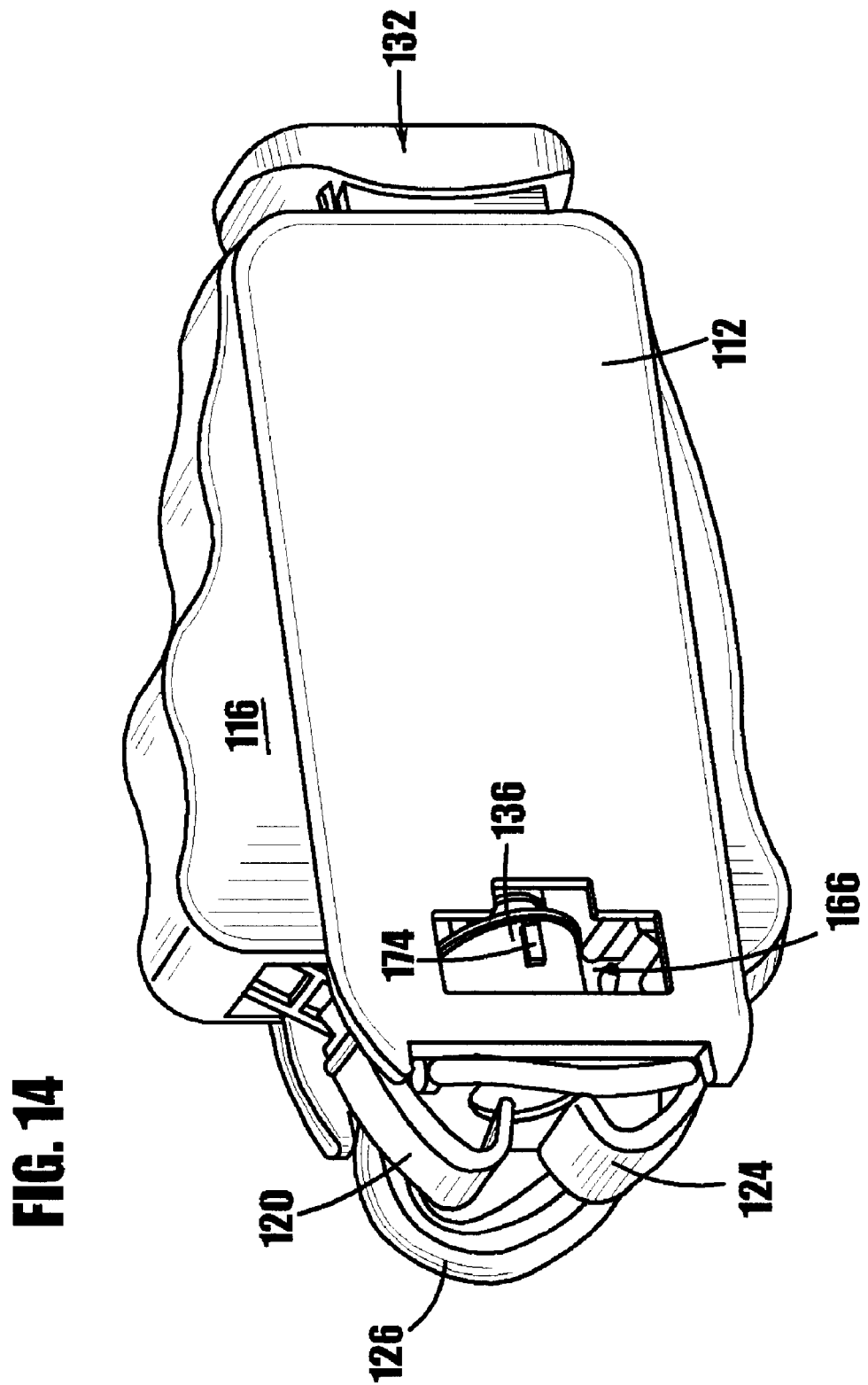
FIG. 14 is a side perspective view of the contact lens applicator of FIG. 10 with the base replaced and a cartridge inserted within the cartridge chamber and ready for application.
Figure 15:
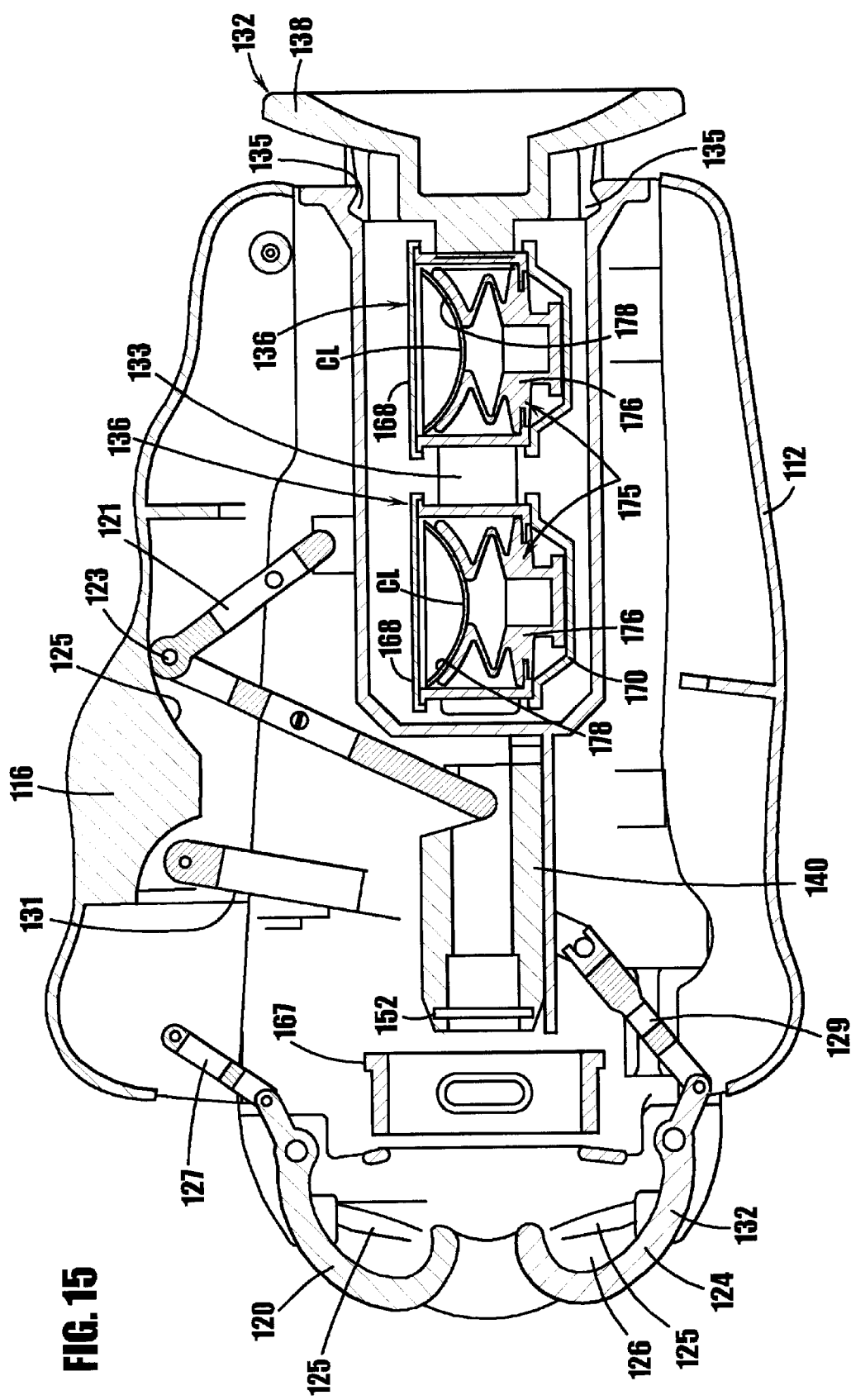
FIG. 15 is a cross-sectional view of the contact lens applicator of FIG. 10 without a cartridge received within the cartridge chamber and the pusher in the retracted position.

In order to load the applicator 110, the base assembly 132 is removed to access the cartridges 136 held thereto. Each cartridge 136 has a handle 174 and a removable top cover 168 and bottom cover 170. As best seen in FIGS. 13 and 14, upon removing the top and bottom covers 168 and 170, the desired cartridge 136 is inserted into the aperture 166 of the housing 112. As best seen in FIG. 15, a frame 113 is mounted to the housing 112 within the aperture 166 and cartridge mount 167 to receive and retain the vial 172 of the cartridge.

When the trigger 116 is depressed, the contact lens CL extends out of the open proximal end 122 for engagement with the user's eye (see FIG. 11). In order to store contact lenses CL for later use, the cartridges 136 can be secured to the flexible sleeve 133 of the base assembly 132 while the base assembly 132 is inserted into the housing 112. As best seen in FIG. 15, deflectable locking fingers 135 on the base assembly 132 secure the base assembly 132 to the housing 112.

Figure 16:
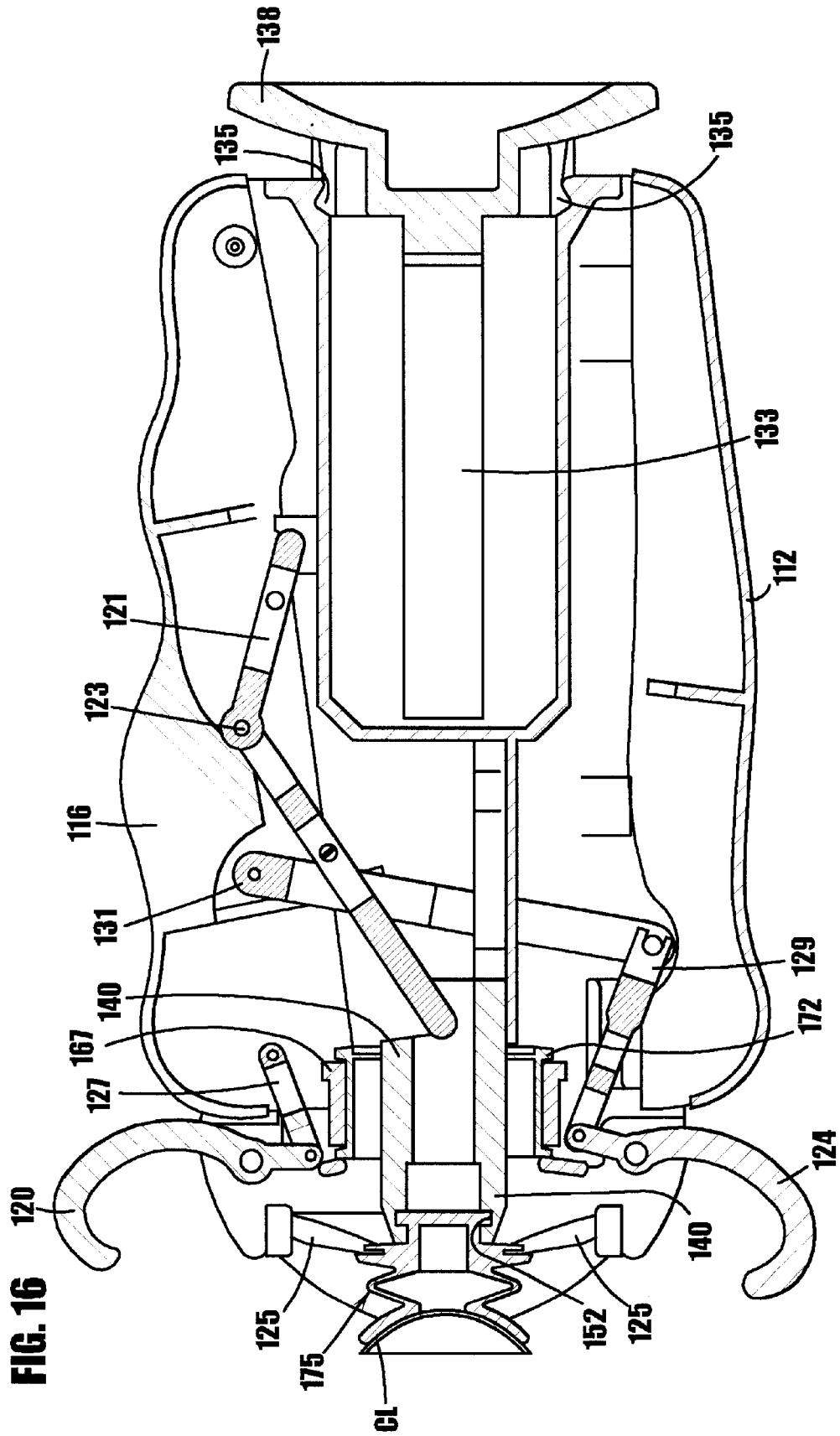
FIG. 16 is a cross-sectional view of the contact lens applicator of FIG. 10 in the extended position with a contact lens ready for insertion in an eye.

Referring now to FIGS. 15 and 16, the open proximal end 122 of the housing 112 is narrowed by a neck 125. As shown in FIG. 16, the neck 125 engages the lens holder 175 to retain the lens holder 175 in the extended position and after withdrawal of the pusher 140. A linkage 121 connects the trigger 116 to the pusher 140, wherein the linkage 121 is hinged at one end to the housing 112 and to the pusher 140 at the other end. Intermediate the ends of the linkage 121 is a hinge 123 for engaging a camming surface 125 formed on the trigger 116. A link 127 connects the trigger 116 to the upper curved cantilever 120 in the drawing while a link/cross link combination 129, 131 connects the lower curved cantilever 124 in the drawing to the trigger 116. When the trigger 116 is squeezed, the linkage 121 is extended to force the pusher 140 and thereby the lens holder 175 outward of the interior of the housing 112. Simultaneously, the link 127 and the link/cross link combination 129, 131 act upon the eyelid depressors 120 and 124, respectively, to pivot the depressors radially outward. Preferably, the eyelid depressors 120 and 124 are fabricated from or coated with an elastomeric material or other non-slip surface to facilitate gently engaging and moving the facial tissue and retaining the eye open. As the eye is retained open, further depression of the trigger 116 also forces the pusher 140 outward to move the lens holder 175 outward and gently deposit the contact lens CL against the eye.

Figure 17A:
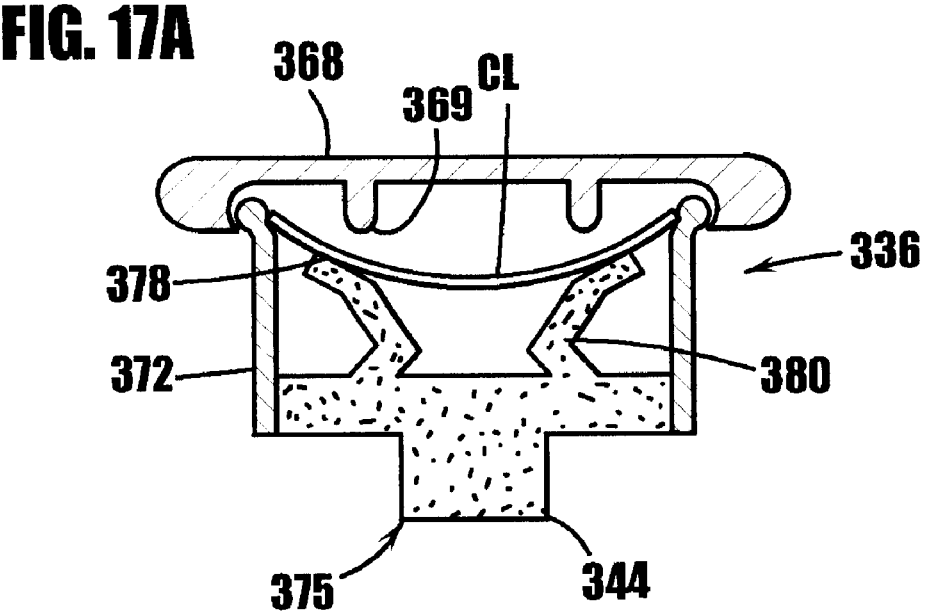
FIG. 17A is a somewhat schematic, cross-sectional view illustrating a cartridge of the contact lens applicator of the invention, including a cover connected to a vial, and a lens holder mounted within the vial.
Figure 17B:
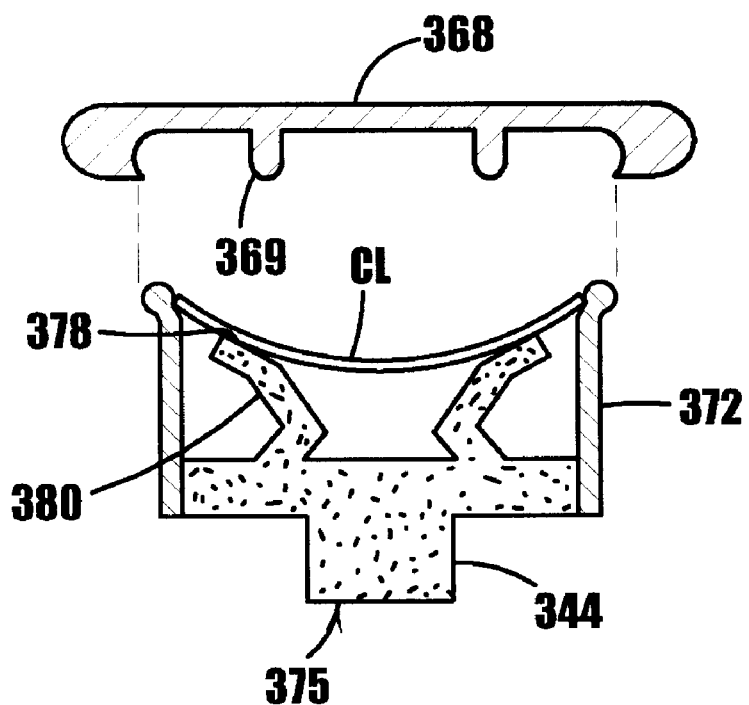
FIG. 17B is a somewhat schematic, cross-sectional view illustrating the cartridge of FIG. 17A, including the cover disconnected from the vial.

For another example, FIGS. 17A and 17B illustrate another version of a contact lens cartridge 336. The cartridge 336 includes a vial 372 which defines an interior having open proximal and distal ends. A lens holder 375 mounts within the vial 372 to seal the distal end and a cover 368 attaches to seal the proximal end. The lens holder includes a lens supporting surface 378 supported by a flexible portion 380. A protrusion 344 extends from the lens supporting surface to facilitate engagement with a pusher or like device. The cover 368 includes an inner ring 369 for stabilizing the contact lens CL when placed upon the lens supporting surface 378. In one embodiment, a bottom cover is not necessary because the lens holder 375 would seal the opposing end of the vial 372. In another embodiment, the cartridge 336 includes a bottom cover for sealing the vial 372. In the latter embodiment, the base portion of the lens holder may define one or more apertures to allow the saline or other solution contained therein to drain out upon removal of the covers.

Turning to FIGS. 18 through 21, another contact lens cartridge embodying the present invention is indicated generally by the reference numeral 436. The cartridge 436 is substantially the same as the cartridge 36 described above, and therefore like reference numerals preceded by the numeral "4", or the numeral "5" instead of the numeral "1", are used to indicate like elements. The primary difference of the cartridge 436 in comparison to the cartridge 36 is that the cartridge 436 comprises a relatively large handle 474 including a neck 477 extending laterally from the vial 472, and a laterally-extending cross-piece 479 forming an approximately T-shaped handle. In addition, the base 476 of the lens holder 475 defines a plurality of through holes 500 angularly spaced about the base relative to each other to allow fluid to drain from the chamber 482 downwardly therethrough.

Figure 19:
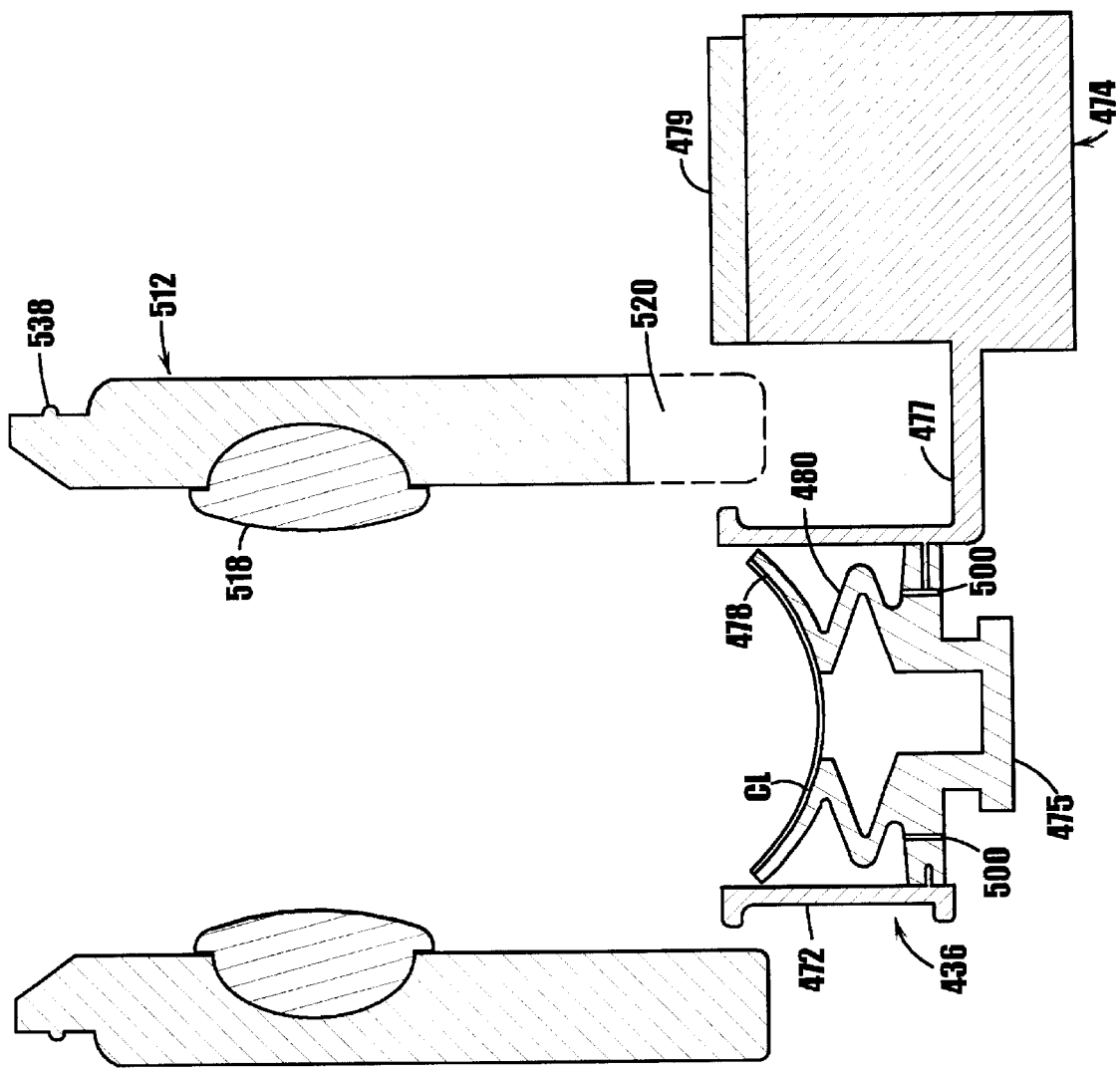
FIG. 19 is a somewhat schematic, cross-sectional view of the cartridge prior to insertion into the cartridge holder of FIG. 18.
Figure 20:
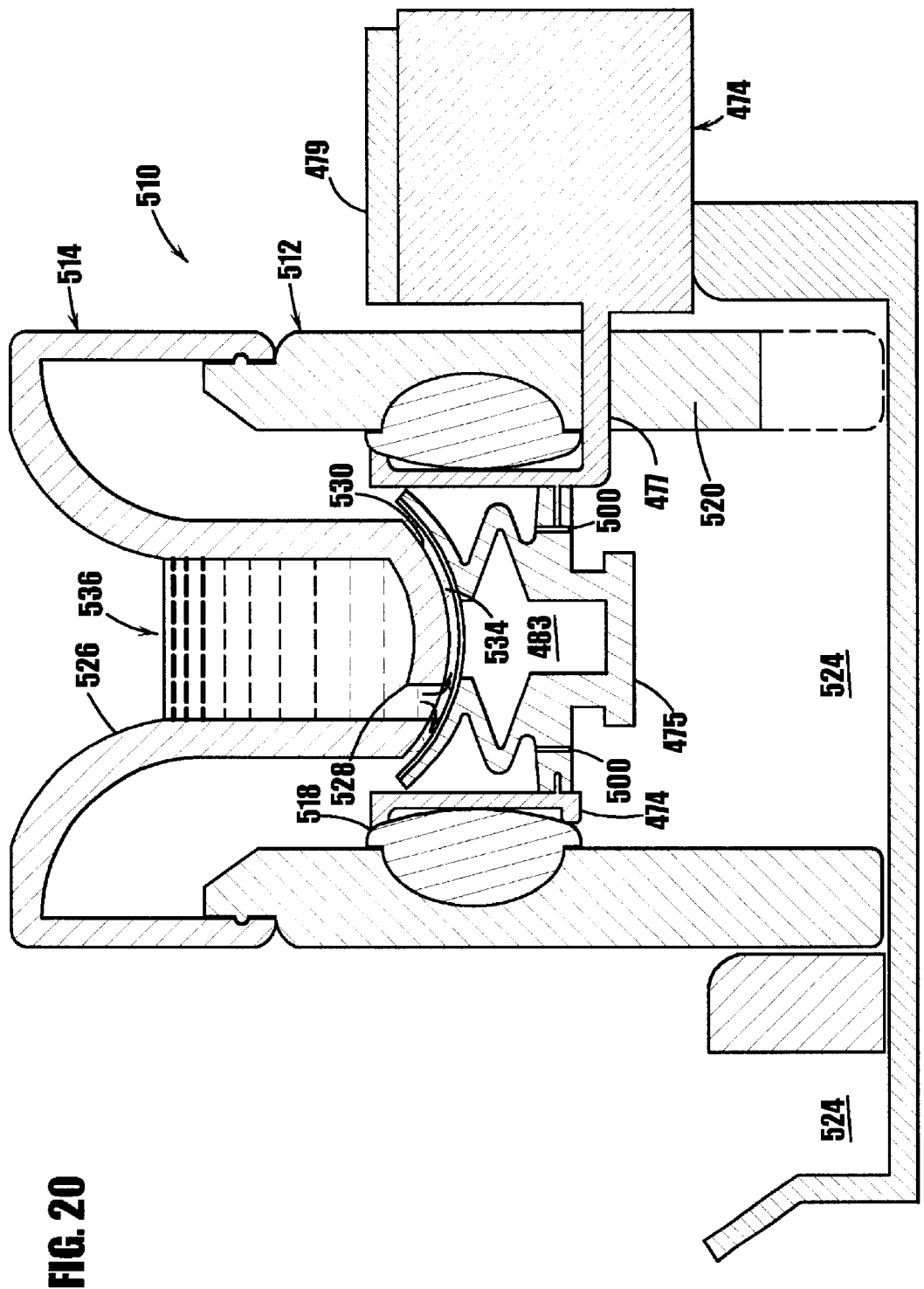
FIG. 20 is a somewhat schematic, cross-sectional view of the cartridge and system of FIG. 18 illustrating the introduction of a cleaning, disinfecting and/or storage solution onto the contact lens seated within the cartridge.

The cartridge 436 is adapted for use with a cleaning and storage system 510 provided for holding the cartridge 436 and cleaning, disinfecting, and/or storing the contact lens CL contained within the cartridge for reuse. The cleaning and storage system 510 includes a cartridge holder 512, a cap 514 and a base 516. The cartridge holder 512 defines an approximately cylindrical shape and includes an annular-extending cartridge mount 518 for locating and frictionally retaining the cartridge within the holder. In the illustrated embodiment, the cartridge mount 518 is formed of a resilient material, such as an elastomer, that frictionally engages the peripheral wall of the vial 472 and releasably secures the vial within the holder. The cartridge holder 512 defines an axially-extending slot 520 for slidably receiving therethrough the neck 477 of the cartridge handle 474. The slot 520 may extend along the entire axial length of the cartridge holder 512, or may extend from either the upper or lower end of the cartridge holder along only a portion of the axial length of the holder. As shown in FIGS. 19 and 20, the cartridge 436 is inserted into the cartridge holder 512 by gripping the handle 474 and inserting the vial 472 into the holder by sliding the neck 477 of the handle through the slot 520 until the vial is frictionally received within the cartridge mount 518.

The base 516 defines a peripheral wall 522 extending about the periphery of the base of the cartridge holder 512 for slidably receiving therein the cartridge holder. As can be seen, the base 516 defines a fluid chamber 524 for receiving the cleaning solution or other fluid passing over the contact lens CL, as described further below.

The cap 514 includes an inwardly extending funnel 526 defining a feed hole 528 formed at the base 530 of the funnel for introducing a predetermined amount of cleaning solution or other fluid over the contact lens CL. The base 530 of the funnel 526 defines an approximately convex surface 532 facing the contact lens CL, and as indicated in broken lines in the Figures, the convex surface 532 may define a plurality of spaced protuberances 534 for maintaining a gap between the convex surface and contact lens to allow the flow of fluid therethrough. In the illustrated embodiment, the cap 514 is snap fit to the cartridge holder 512 by means of an annular protuberance formed on the cartridge holder and a corresponding annular recess 538 formed on the cap. However, as may be recognized by those of ordinary skill in the pertinent art based on the teachings herein, the cap may be releasably coupled to the holder in any of numerous different ways that are currently or later become known for performing this function.

Figure 18:
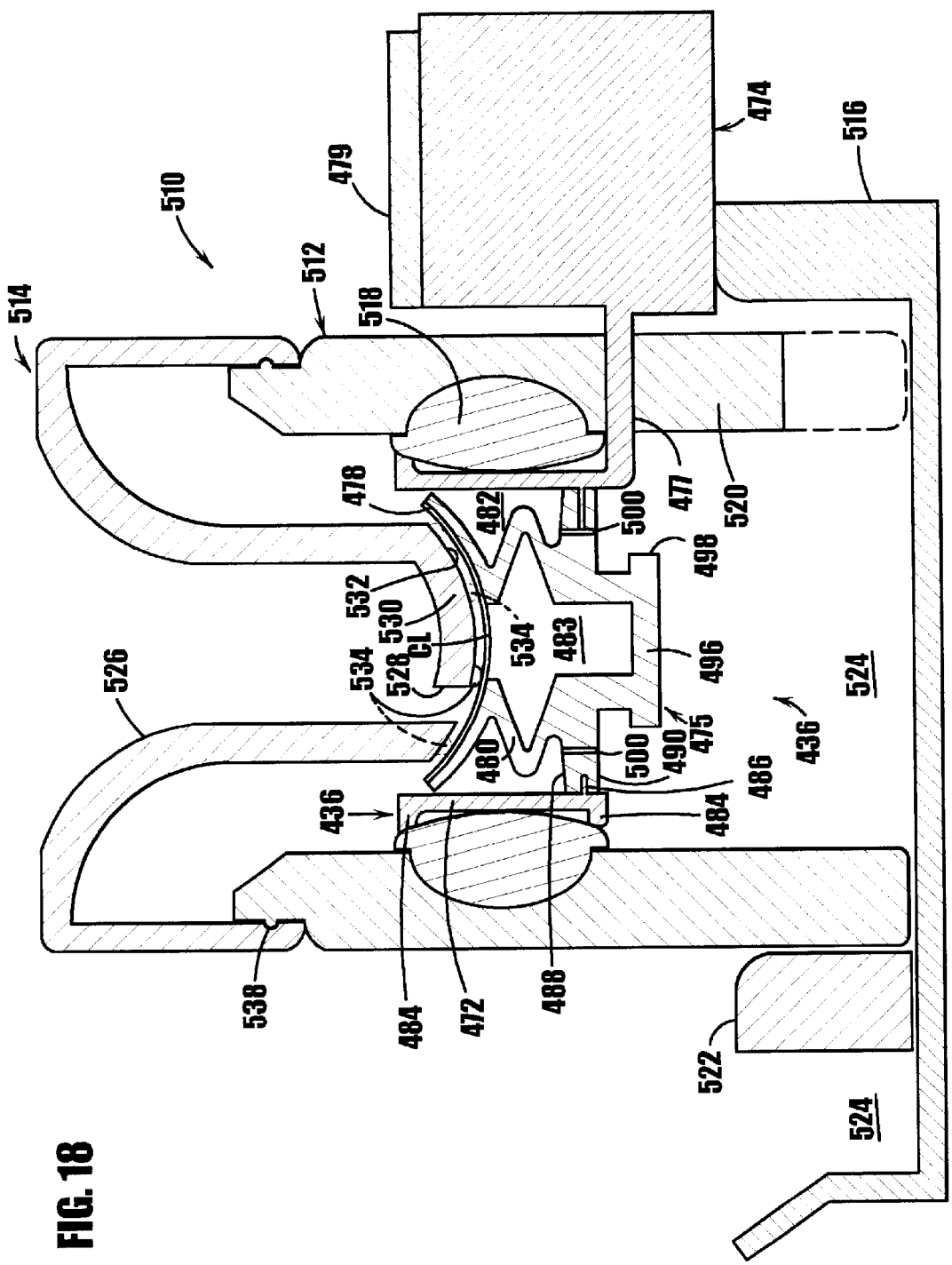
FIG. 18 is a somewhat schematic, cross-sectional view another embodiment of a contact lens cartridge mounted within a cleaning, disinfecting and/or storage system of the invention.

In the operation of the system 510, the cartridge 436 including the contact lens CL seated on the lens support surface 478 is mounted within the cartridge holder 512, the cartridge holder is seated within the base 516, and the cap 514 is secured to the holder. As shown in FIG. 18, the convex surface 532 and protuberances 534 of the cap 514 substantially prevent movement of the lens CL relative to the lens support surface 478 upon securing the cap to the holder.

Figure 21:
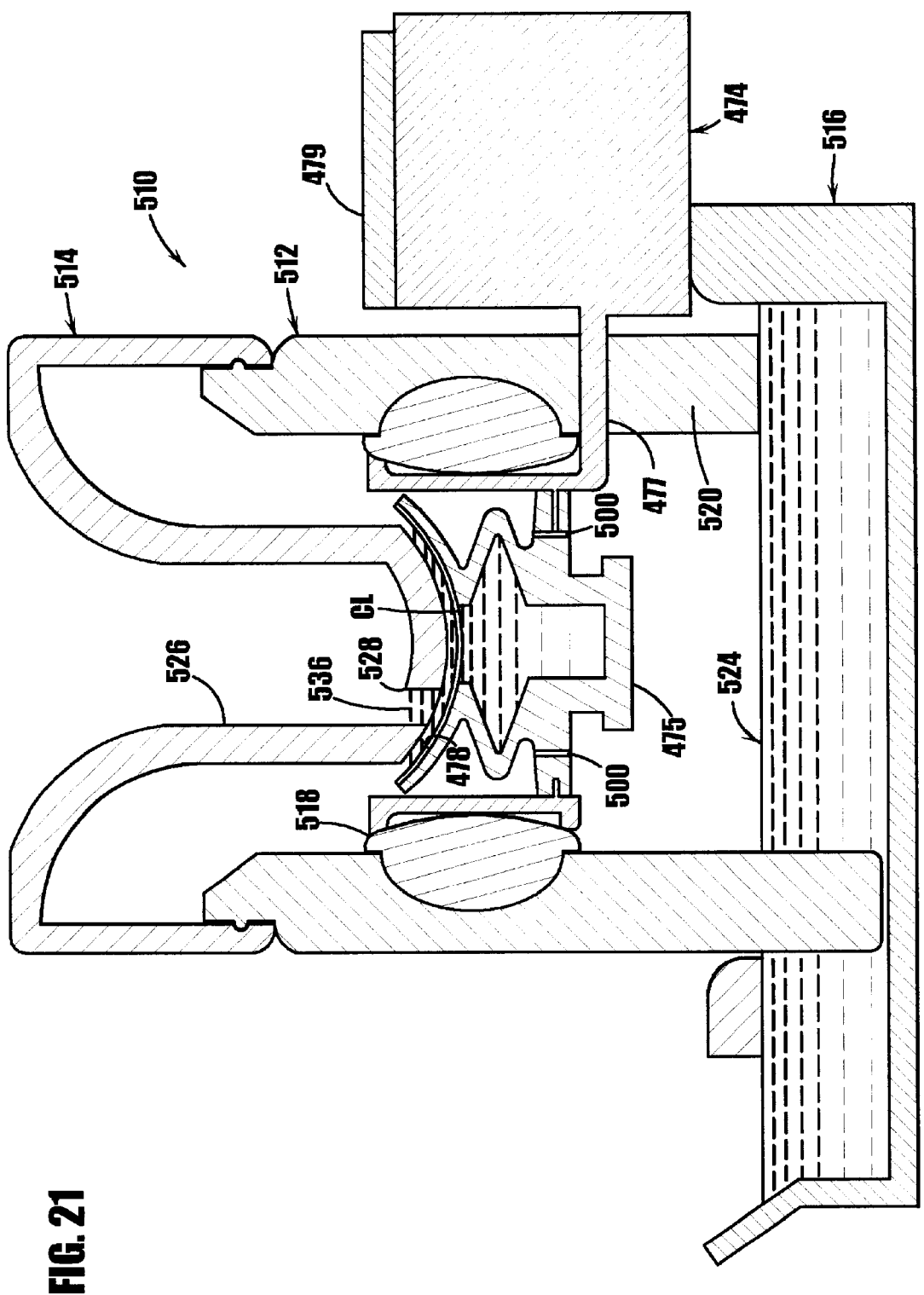
FIG. 21 is a somewhat schematic, cross-sectional view of the cartridge and system of FIG. 18 illustrating the condition of the liquid solution during storage of the lens.

Then, as shown in FIG. 20, the user dispenses a predetermined amount of fluid 536 into the funnel 526 of the cap. The fluid 536 may take the form of any of numerous different fluids that are currently or later become known for purposes of cleaning, disinfecting and/or storing contact lenses. For example, the fluid may take the form of a commercially-available "multipurpose" solution and/or a sterile saline solution. In the illustrated embodiment, the volume of the funnel 526 is selected to hold a predetermined volume of fluid for purposes of cleaning, disinfecting and/or storing the contact lens CL. If desired, the funnel 526 may define a plurality of graduations with appropriate measuring indicia thereon for purposes of measuring the quantity of fluid dispensed into the funnel. As shown in FIG. 20, upon filling the funnel 526, the fluid 536 flows through the feed hole 528 and radially outwardly through the gap formed between the contact lens CL and the convex surface 532. The continuously flowing fluid 536 serves to thoroughly clean the contact lens. As may be recognized by those skilled in the pertinent art based on the teachings herein, the size of the feed hole 528 may be selected to control the flow rate of fluid therethrough and over the surfaces of the lens. In addition, the funnel may include a piston reciprocally mounted therein (not shown) for forcing the fluid within the funnel through the feed hold 528 and onto the contact lens. As described above in connection with the previous embodiments, the lens support surface 478 of the lens holder preferably defines a plurality of spaced protuberances or other surface discontinuities not only to facilitate release of the lens from the lens holder as described above, but to allow the fluid 536 to flow between the lens and lens support surface and downwardly into the chamber 483 of the lens holder. The remainder of the fluid passing over the lens holder 475 flows through the apertures 500 of the lens holder and downwardly into the chamber 524 of the base. As shown in FIG. 21, upon draining the funnel 526, the fluid 536 fills the gap between the convex surface 532 and contact lens CL, and flows into the chamber 483 of the lens holder to thereby continue to clean and/or disinfect the lens, and the remainder of the fluid drains into the chamber 524 of the base.

Once the lens is cleaned and/or disinfected, the cartridge 436 may be removed from the system 510 by lifting the cartridge holder 512 away from the base 516 and/or removing the cap 514 from the base. Then, the neck 477 of the cartridge may be moved either upwardly or downwardly through the slot 520 to remove the cartridge from the holder. The cartridge may then be inserted into the cartridge apertures 66, 166 of the applicators 10, 110 described above for insertion of the cleaned and/or disinfected lens CL onto a user's eye. Alternatively, suitable caps (not shown) may be attached to the upper and lower ends of the vial 472 to seal the contact lens CL within the vial, and the cartridge may in turn be stored within the housing of the applicator in a manner similar to that described above.

As may be recognized by those skilled in the pertinent art based on the teachings herein, numerous changes and modifications may be made to the above-described and other embodiments of the present invention without departing from the spirit and scope of the invention as defined by the appended claims. For example, the contact lenses may be supplied by the manufacturers pre-packaged in the cartridges. Alternatively, the end users may insert the contact lens into the cartridge and then apply the lens to the eye using the applicator of the invention. In still another embodiment, the contact lens is sealed within the applicator and the applicator is disposed of after use. Similarly, the lens holder may take any of numerous different shapes and/or configurations. For example, the surface of the lens holder may define any of numerous different surface configurations and/or discontinuities to facilitate release of the lens from the lens holder onto the eye. In addition, the eyelid depressors or tissue-engaging surfaces may take any of numerous different shapes and/or configurations for purposes of engaging the facial tissue and retaining the eye open during application of the contact lens thereto. Similarly, the trigger or like actuating member(s) may take any of numerous different shapes and/or configurations for purposes of substantially simultaneously or otherwise actuating the tissue-engaging surfaces and the lens holder from the retracted to the extended positions. For example, if desired, the actuator could be driven by an electric motor or a pneumatic drive. Accordingly, this detailed description of preferred embodiments is to be taken in an illustrative as opposed to a limiting sense.

What is claimed is:

1. A contact lens applicator for applying a contact lens to an eye, comprising:
    a housing defining an opening;
    at least one actuating member movably mounted on the housing;
    at least one tissue-engaging surface movably mounted on the housing adjacent to the opening and drivingly coupled to the at least one actuating member for movably engaging tissue adjacent to the eye upon actuating the at least one actuating member and retaining the eye open during application of the contact lens thereto;
    a support surface extending outwardly of the housing adjacent to the at least one tissue-engaging surface for supporting the applicator against the facial tissue adjacent to the eye during application of the contact lens thereto; and
    a lens moving member movably mounted on the housing and drivingly coupled to the at least one actuating member for movement between a retracted position and an extended position for applying the contact lens coupled thereto to the eye, wherein actuation of the at least one actuating member substantially simultaneously actuates the at least one tissue-engaging surface and the lens moving member to thereby retain the eye open and apply the contact lens thereto.

2. A contact lens applicator as defined in claim 1, wherein the at least one tissue-engaging surface includes first and second curved cantilevers movably mounted on the housing on approximately opposite sides of the opening relative to each other, and drivingly coupled to the at least one actuating member for movably engaging the tissue adjacent to the eye upon actuating the at least one actuating member and retaining the eye open during application of the contact lens thereto.

3. A contact lens applicator as defined in claim 1, wherein the at least one tissue-engaging surface includes a roller.

4. A contact lens applicator as defined in claim 3, further comprising a rack and pinion coupled between the at least one actuating member and the roller, such that the rack meshes with the pinion to rotate the roller upon actuating the at least one actuating member.

5. A contact lens applicator as defined in claim 1, wherein the at least one actuating member is pivotally mounted on the housing and includes an actuating surface, and the lens moving member includes a cam surface engageable with the actuating surface upon pivoting the actuating member to thereby move the lens moving member between the retracted and extended positions.

6. A contact lens applicator as defined in claim 1, wherein the housing defines a chamber for receiving a cartridge which stores the contact lens.

7. A contact lens applicator as defined in claim 6, further comprising a cartridge holder defining at least one mounting surface for releasably mounting at least one cartridge thereon, and wherein the cartridge holder is connectable to the housing with the at least one mounting surface receivable within the housing chamber for storing the least one cartridge mounted thereon within the housing.

8. A contact lens holder as defined in claim 7, wherein the cartridge holder defines a platform for supporting the applicator in an upright position during application of a contact lens to the eye.

9. A contact lens applicator as defined in claim 1, further comprising at least one biasing member coupled to the lens moving member for biasing the lens moving member in a retracted position.

10. A contact lens applicator as defined in claim 1, wherein the lens moving member is contained substantially within the housing and moves substantially axially therethrough.

11. A contact lens applicator as defined in claim 1, further comprising at least one cartridge for storing a contact lens, wherein the cartridge includes:
    a body defining an interior for receiving therein the contact lens; and
    a contact lens holder slidably mounted within the body and defining a lens support surface for supporting the contact lens thereon, wherein the contact lens holder is connectable to the lens moving member and movable therewith between the retracted and extended positions for applying the contact lens to the eye.

12. A contact lens applicator as defined in claim 11, wherein the lens holder includes a flexible lens support surface and a base releasably connected to the body, and the lens holder is movable out of the body upon actuating the lens moving member between the retracted and extended positions.

13. A contact lens applicator as defined in claim 1, wherein the support surface is defined by at least one support member pivotally mounted on the housing.

14. A contact lens applicator as defined in claim 1, wherein the support surface conformably contacts the facial tissue adjacent to the eye.

15. A cartridge for storing a contact lens, the cartridge being mountable on a contact lens applicator having a lens moving member, an actuator for moving the lens moving member between a retracted and an extended position for applying a contact lens stored in the cartridge to an eye, and at least one tissue-engaging surface drivingly connected to the actuator for engaging facial tissue adjacent to an eye and retaining the eve open during application of a contact lens thereto, the cartridge comprising:
    a body mountable to the applicator and defining an interior for receiving therein the contact lens; and
    a contact lens holder received within the interior of the body and defining a lens support surface for supporting the contact lens thereon and movable with the lens moving member between the retracted and extended positions and with the at least one tissue-engaging surface for engaging facial tissue adjacent to an eye for applying the contact lens to the eye.

16. A cartridge as recited in claim 15, wherein the contact lens holder includes a flexible portion coupled to the lens support surface.

17. A cartridge as defined in claim 16, wherein the lens support surface defines a plurality of surface discontinuities thereon for facilitating release of the lens from lens support surface and onto an eye.

18. A cartridge as defined in claim 17, wherein the surface discontinuities include a plurality of angularly spaced protuberances.

19. A cartridge as recited in claim 16, wherein the flexible portion of the contact lens holder is defined by a bellows.

20. A cartridge as recited in claim 15, further comprising a contact lens on the lens supporting surface, a solution within the body immersing the contact lens, and at least one cover for selectively sealing the interior of the body, wherein the at least one cover is removable prior to installing the cartridge into an applicator to dispense the contact lens therefrom onto an eye.

21. A cartridge as recited in claim 15, wherein the lens holder is slidably mounted within the body.

22. A cartridge for storing a contact lens, the cartridge being mountable on a contact lens applicator having a lens moving member, and an actuator for moving the lens moving member between a retracted and an extended position for applying a contact lens stored in the cartridge to an eye, the cartridge comprising:
   a body mountable to the applicator and defining an interior for receiving therein the contact lens; and
   a contact lens holder received within the interior of the body and defining a lens support surface for supporting the contact lens thereon and movable upon actuation of the actuator with the lens moving member between the retracted and extended positions for applying the contact lens to an eye, wherein the contact lens holder includes a flexible portion coupled to the lens support surface, and defines a fluid chamber within the flexible portion and underlying a contact lens seated on the lens support surface, and wherein the flexible portion is compressible with movement of the lens moving member of the applicator to cause fluid within the fluid chamber to flow between the lens and lens support surface and facilitate release of the lens therefrom.

23. A cartridge for storing a contact lens comprising:
   a body defining an interior for receiving therein the contact lens;
   a contact lens holder slidably mounted within the body and defining a lens support surface for supporting the contact lens thereon;
   a contact lens on the lens supporting surface, a solution within the body immersing the contact lens, and at least one cover for selectively sealing the interior of the body, wherein the at least one cover is removable prior to installing the cartridge into an applicator to dispense the contact lens therefrom onto an eye; and
   wherein the contact lens holder is engageable with a lens moving member of an applicator for moving the lens holder and lens out of the body and onto an eye, and the body defines a rib and the contact lens holder includes a pair of annular flanges defining a channel therebetween, the channel being sized and configured to receive the rib, and the contact lens holder further includes an outwardly extending protrusion with an annular rim for engaging the lens moving member.

24. A cartridge for storing a contact lens comprising:
   a body defining an interior for receiving therein the contact lens;
   a contact lens holder slidably mounted within the body and defining a lens support surface for supporting the contact lens thereon;
   a contact lens on the lens supporting surface and a solution within the body immersing the contact lens; and
   an upper cover and a lower cover, each releasably connectable to the body for sealing the contact lens and fluid therein, and wherein the lens holder defines at least one aperture formed therethrough to allow fluid within the interior of the body to drain therefrom upon removal of at least one of the upper and lower covers from the body.

25. A cartridge for storing a contact lens in combination with an applicator for delivering a contact lens into an eye, wherein the cartridge comprises:
   a body defining an interior for receiving therein the contact lens; and
   a contact lens holder movably mounted within the body and defining a lens support surface for supporting the contact lens thereon; and
   wherein the applicator comprises:
      a body having an open proximal end and a distal end, and defining an interior;
      a cartridge mount for supporting the cartridge and lens seated therein adjacent to the open proximal end;
      a pusher housed within the interior and movable along an axis defined by the body for extending the lens support surface and thereby the contact lens into the eye;
      a member mounted to the body for actuating the pusher; and
      at least one depressor drivingly connected about the open proximal end of the body and operatively connected to the member such that as the pusher is moved by the member the at least one depressor retains at least one eyelid open.

26. A contact lens applicator for applying a contact lens to an eye, comprising:
   first means forming an opening for passage of the contact lens therethrough;
   second means mounted on the first means for actuating the contact lens applicator;
   third means coupled to the second means for movably engaging tissue adjacent to the eye upon actuating the second means and retaining the eye open during application of the contact lens thereto;
   fourth means for supporting the applicator against the facial tissue adjacent to the eye during application of the contact lens thereto; and
   fifth means coupled to the second means for holding the contact lens and movable between a retracted position and an extended position for applying the contact lens coupled thereto to the eye, wherein actuation of the second means simultaneously actuates the third and fifth means to thereby retain the eye open and apply the contact lens thereto.

27. A contact lens applicator as recited in claim 26, wherein the first means is a housing.

28. A contact lens applicator as recited in claim 26, wherein the second means is at least one actuating member.

29. A contact lens applicator as recited in claim 26, wherein the third means is at least one tissue-engaging surface.

30. A contact lens applicator as recited in claim 29, wherein the at least one tissue-engaging surface is defined by two curved cantilevers for retaining an upper eyelid and a lower eyelid, respectively.

31. A contact lens applicator as recited in claim 29, wherein the at least one tissue-engaging surface is defined by two rollers for retaining an upper eyelid and a lower eyelid, respectively.

32. A contact lens applicator as recited in claim 26, wherein the fourth means is a support surface.

33. A contact lens applicator as defined in claim 32, wherein the support surface is defined by a pair of arcuate bands extending outwardly of an open proximal end of the first means to form an eyecup for locating the applicator against an eye.

34. A contact lens applicator as recited in claim 26, wherein the fifth means is a lens moving member.

35. A contact lens applicator as recited in claim 26, further comprising a base removably coupled to a distal end of the first means for providing access to the interior and retaining at least one cartridge therein for storing a contact lens.

36. A method for applying a contact lens to an eye, comprising the following steps:

providing a contact lens cartridge including a body and a lens holder movable within the body;

providing a contact lens in a substantially aseptic condition on the lens holder;

providing an applicator including a surface for mounting the contact lens cartridge, a lens moving member, at least one actuator for moving the lens moving member between a retracted and an extended position, and at least one tissue-engaging surface drivingly coupled to the at least one actuator and movably mounted on the applicator;

mounting the cartridge with the lens on the applicator;

placing the eye adjacent to the applicator and the at least one tissue-engaging surface into contact with facial tissue adjacent to the eye;

actuating the at least one actuator and moving the at least one tissue-engaging surface against facial tissue adjacent to the eye to retain the eye open and moving the lens moving member from the retracted to the extended position and, in turn, moving the lens holder with the lens mounted thereon from a retracted to an extended position into contact with the eye; and releasing the contact lens from the lens holder to the eye.

37. A method as recited in claim 36, further comprising placing two tissue-engaging surfaces into contact with facial tissue on the upper and lower sides of the eye to retain the eye open during application of the contact lens thereto.

38. A method as recited in claim 36, providing a lens holder including a fluid chamber between the lens and a base portion of the lens holder, providing a solution in the chamber, and causing solution in the chamber to flow between the lens and lens holder to facilitate release of the lens therefrom and onto the eye.

39. A method as recited in claim 36, comprising the step of providing the contact lens sealed in an aseptic condition within the cartridge.

40. A method as recited in claim 36, comprising the step of providing a re-usable contact lens cartridge for storing a contact lens in the cartridge after removal of the lens from an eye.

41. A method for applying a contact lens to an eye, comprising the following steps:

providing a contact lens cartridge including a body and a lens holder movable within the body;

providing a contact lens in a substantially aseptic condition on the lens holder;

providing an applicator including a surface for mounting the contact lens cartridge, a lens moving member, an actuator for moving the lens moving member between a retracted and an extended position, and at least one tissue-engaging surface drivingly coupled to the actuator and movably mounted on the applicator;

mounting the cartridge with the lens on the applicator;

placing the at least one tissue-engaging surface into contact with the facial tissue adjacent to the eye; and substantially simultaneously actuating the at least one tissue-engaging surface and the lens moving member and, in turn, retaining the eye open with the at least one tissue-engaging surface and releasing the lens from the lens holder onto the eye.

42. A contact lens applicator for applying a contact lens to an eye, comprising:

a body;

at least one actuator mounted on the body;

at least one tissue-engaging surface drivingly coupled to the actuator for engaging tissue adjacent to the eye upon actuating the actuator to facilitate retaining the eye open during application of the contact lens thereto;

a support surface coupled to the body for supporting the applicator adjacent to the eye during application of the contact lens thereto; and a lens moving member drivingly coupled to the at least one actuator for movement between a retracted position and an extended position for applying a contact lens coupled thereto to the eye, wherein the at least one actuator actuates the at least one tissue-engaging surface to facilitate retaining the eye open and actuates the lens moving member to apply the contact lens coupled thereto to the open eye.

43. A contact lens applicator as recited in claim 42, wherein the at least one tissue-engaging surface is selected from a roller rotatably mounted on the body, and a curved member pivotally mounted on the body.

44. A contact lens applicator as defined in claim 42, further comprising at least one biasing member coupled to the lens moving member for biasing the lens moving member toward a retracted position.

45. A contact lens applicator as defined in claim 42, further comprising a cartridge mountable on the body and including a cartridge body, and a contact lens holder movably mounted within the cartridge body and drivingly connectable to the lens moving member for movement therewith between retracted and extended positions.

46. A cartridge for storing a contact lens, the cartridge being mountable on a contact lens applicator having a lens moving member, an actuator for moving the lens moving member between a retracted and an extended position for applying a contact lens stored in the cartridge to an eye, and at least one tissue-engaging surface drivingly connected to the actuator for engaging facial tissue adjacent to an eye and retaining the eye open during application of a contact lens thereto, the cartridge comprising:

first means for receiving and storing therein the contact lens; and second means received within the first means for supporting the contact lens thereon and movable with the lens moving member of the applicator between the retracted and extended positions and with the at least one tissue-engaging surface for engaging facial tissue adjacent to an eye for applying the contact lens to an the eye.

47. A cartridge as recited in claim 46, wherein the first means is a body defining an interior chamber for receiving therein the contact lens.

48. A cartridge as recited in claim 46, wherein the second means is a contact lens holder received within the interior of the first means and defining a lens support surface for supporting the contact lens thereon and movable with the lens moving member of the applicator between the retracted and extended positions for applying the contact lens to an eye.

49. A cartridge as defined in claim 48, wherein the lens support surface defines a plurality of surface discontinuities thereon for facilitating release of the lens from lens support surface and onto an eye.

50. A cartridge as defined in claim 49, wherein the surface discontinuities include a plurality of angularly spaced protuberances.

51. A cartridge as recited in claim 48, further comprising a contact lens on the lens supporting surface, a solution within the first means immersing the contact lens, and at least one cover for selectively sealing the interior of the first means, wherein the at least one cover is removable prior to installing the cartridge into an applicator to dispense the contact lens therefrom onto an eye.

52. A cartridge as recited in claim 46, wherein the contact lens holder includes a base portion drivingly connectable to the lens moving member and movable therewith between retracted and extended positions, and a flexible portion extending between the lens support surface and the base portion.

53. A cartridge as recited in claim 52, wherein the flexible portion is defined by a bellows.

54. A cartridge for storing a contact lens, the cartridge being mountable on a contact lens applicator having a lens moving member, and an actuator for moving the lens moving member between a retracted and an extended position for applying a contact lens stored in the cartridge to an eye, the cartridge comprising:
   first means for receiving and storing therein the contact lens; and
   a contact lens holder received within the first means for supporting the contact lens thereon, wherein the contact lens holder includes a base portion drivingly connectable to the lens moving member and movable therewith between retracted and extended positions, and a flexible portion extending between the lens support surface and the base portion, and wherein at least one of the base and flexible portion defines a chamber for receiving a fluid, and the flexible portion is compressible upon moving the contact lens seated on the lens support surface into contact with an eye to cause fluid in the chamber to flow out of the chamber between the lens and lens support surface and, in turn, facilitate release of the lens from the lens support surface and onto the eye.

55. A cartridge for storing a contact lens, the cartridge being mountable on a contact lens applicator having a lens moving member, and an actuator for moving the lens moving member between a retracted and an extended position for applying a contact lens stored in the cartridge to an eye, the cartridge comprising:
   first means for receiving and storing therein the contact lens; and
   a contact lens holder received within the interior of the first means and defining a lens support surface for supporting the contact lens thereon and movable with the lens moving member of the applicator between the retracted and extended positions for applying the contact lens to an eye;
   a contact lens on the lens supporting surface, a solution within the first means immersing the contact lens, and at least one cover for selectively sealing the interior of the first means, wherein the at least one cover is removable prior to installing the cartridge into the applicator to dispense the contact lens therefrom onto an eye; and
wherein the lens holder defines at least one aperture for releasing solution therethrough and out of the cartridge prior to applying the contact lens to an eye.

56. An apparatus comprising:
   a cartridge for storing a contact lens, the cartridge being mountable on a contact lens applicator having a lens moving member, and an actuator for moving the lens moving member between a retracted and an extended position for applying a contact lens stored in the cartridge to an eye, the cartridge comprising:
      a body mountable to the applicator and defining an interior for receiving therein the contact lens; and
      a contact lens holder received within the interior of the body and defining a lens support surface for supporting the contact lens thereon and movable upon actuation of the actuator with the lens moving member between the retracted and extended positions for applying the contact lens to an eye; and
   an apparatus for cleaning a contact lens within the cartridge, the apparatus comprising:
      a body mount for supporting the cartridge body thereon;
      a cover mounted on the body mount and overlying the contact lens holder and contact lens seated on the lens support surface thereof, wherein the cover defines an inlet aperture coupled in fluid communication with the interior of the body and the lens seated on the lens support surface for introducing a solution through the aperture and into contact with the lens on the lens support surface.

57. An apparatus within the cartridge as recited in claim 56, wherein the cover defines a surface overlying the contact lens seated on the lens support surface, and a plurality of protuberances spaced relative to each other on said surface for maintaining a gap between said surface and the contact lens.

58. An apparatus as recited in claim 56, wherein the cover defines a substantially convex surface overlying the contact lens seated on the lens support surface.

59. An apparatus as recited in claim 56, wherein the cover defines an external fluid chamber located on an external side of the aperture and coupled in fluid communication with the aperture for receiving a fluid and allowing the fluid to flow through the aperture and into the interior of the body.

60. A method for applying a contact lens to an eye, comprising the following steps:
   providing an applicator including a lens holder, a lens moving member drivingly connectable to the lens holder, at least one actuator for moving the lens moving member between a retracted and an extended position, and at least one tissue-engaging surface drivingly coupled to the at least one actuator and movably mounted on the applicator;
   placing a contact lens on the lens holder;
   placing the applicator adjacent to the eye with the at least one tissue-engaging surface in contact with facial tissue adjacent to the eye;
   actuating the at least one actuator to move the at least one tissue-engaging surface against facial tissue adjacent to the eye and retain the eye open, and move the lens moving member from the retracted to the extended position to, in turn, move the lens holder with the lens mounted thereon from a retracted to an extended position into contact with the eye; and releasing the contact lens from the lens holder to the eye.

61. A method as defined in claim 60, further comprising the following steps:

providing a contact lens cartridge including a body and the lens holder movable within the body;

providing a contact lens in a substantially aseptic condition on the lens holder;

mounting the cartridge with the lens on the applicator;

actuating the lens moving member from the retracted to the extended position and, in turn moving the lens holder with the lens mounted thereon from a retracted to an extended position into contact with the eye; and releasing the contact lens from the lens holder to the eye without touching the lens to thereby maintain the aseptic condition of the lens.

* * * * *